(12) United States Patent
Vanderbush et al.

(10) Patent No.: US 7,963,396 B2
(45) Date of Patent: *Jun. 21, 2011

(54) VACUUM PACKAGE SYSTEM

(75) Inventors: Edward Vanderbush, Downingtown, PA (US); Scott Young, Kennett Square, PA (US); Jon Lundquist, Chandler, AZ (US); Ricky Yeager, Douglassville, PA (US); Hiroshi Togashi, Sano (JP)

(73) Assignees: West Pharmaceutical Services, Inc., Lionville, PA (US); Daikyo Seiko, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/510,563

(22) Filed: Jul. 28, 2009

(65) Prior Publication Data

US 2009/0288977 A1    Nov. 26, 2009

Related U.S. Application Data

(63) Continuation-in-part of application No. 12/346,139, filed on Dec. 30, 2008, which is a continuation-in-part of application No. 11/171,814, filed on Jun. 30, 2005, now abandoned.

(60) Provisional application No. 60/584,826, filed on Jul. 1, 2004.

(51) Int. Cl.
 *B65D 25/10* (2006.01)
 *B65D 81/20* (2006.01)
 *B65B 31/00* (2006.01)

(52) U.S. Cl. ............ 206/524.8; 206/438; 206/366

(58) Field of Classification Search ........... 206/524.8, 206/438, 571, 570, 564, 363, 370, 443, 557, 206/563, 560, 365, 366, 559; 211/71.01, 74

See application file for complete search history.

(56) References Cited

U.S. PATENT DOCUMENTS 2,629,421 A    2/1953    Ayres
(Continued)

FOREIGN PATENT DOCUMENTS

JP    2000-95209 A    10/2001
(Continued)

OTHER PUBLICATIONS

Daikyo Seiko, Ltd.; "Company Profile and Catalog;" 12 pages.
(Continued)

*Primary Examiner* — Steven A. Reynolds
(74) *Attorney, Agent, or Firm* — Panitch Schwarze Belisario & Nadel LLP

(57) ABSTRACT

A vacuum packaging system for transporting a plurality of medical containers includes a plurality of medical a tray that receives and supports the medical containers. The tray includes opposing first and second side walls, opposing side and rear walls and a bottom floor. The walls extend generally perpendicularly from the bottom floor of the tray to a top edge thereof. A nesting plate is removably mountable in the tray and includes a plurality of generally cylindrical sleeves each receiving one of the plurality of medical containers. A support surface within the tray generally extends parallel to and spaced a predetermined distance from the bottom floor of the tray and receives and supports the nesting plate. An air impervious flexible film defines an internal cavity and completely surrounds the tray and the medical containers. The internal cavity is evacuated to and maintained at a predetermined vacuum level below atmospheric pressure.

12 Claims, 20 Drawing Sheets

U.S. PATENT DOCUMENTS

| | | | |
|---|---|---|---|
| 2,658,011 A | | 11/1953 | Price |
| 2,771,399 A | | 11/1956 | Savage |
| 3,297,191 A | | 1/1967 | Eastman |
| 3,562,999 A | | 2/1971 | Barbedienne |
| 3,643,812 A | * | 2/1972 | Mander et al. ............... 211/74 |
| 3,677,774 A | | 7/1972 | Rausing |
| 3,746,160 A | | 7/1973 | Thompson et al. |
| 3,747,751 A | | 7/1973 | Miller et al. |
| 3,850,340 A | | 11/1974 | Siemonsen et al. |
| 3,999,661 A | | 12/1976 | Jones |
| 4,154,795 A | | 5/1979 | Thorne |
| 4,365,715 A | | 12/1982 | Egli |
| 4,457,123 A | | 7/1984 | Hoehn |
| 4,523,679 A | | 6/1985 | Paikoff et al. |
| 4,548,824 A | | 10/1985 | Mitchell et al. |
| 4,549,656 A | | 10/1985 | Barnes et al. |
| 4,616,762 A | * | 10/1986 | Alexander ............... 220/658 |
| 4,676,377 A | * | 6/1987 | Rainin et al. ............... 206/508 |
| 4,718,463 A | | 1/1988 | Jurgens, Jr. et al. |
| 4,730,730 A | | 3/1988 | Clarkson |
| 4,754,595 A | | 7/1988 | Sanderson |
| 4,936,449 A | | 6/1990 | Conard et al. |
| 5,014,494 A | | 5/1991 | George |
| 5,035,323 A | | 7/1991 | Daniels et al. |
| 5,069,594 A | | 12/1991 | Bott et al. |
| 5,372,252 A | | 12/1994 | Alexander |
| 5,426,922 A | | 6/1995 | Bott et al. |
| 5,439,132 A | | 8/1995 | Gorlich |
| 5,456,360 A | * | 10/1995 | Griffin ............... 206/443 |
| 5,477,663 A | | 12/1995 | Smith et al. |
| 5,622,676 A | | 4/1997 | Lind |
| 5,642,816 A | * | 7/1997 | Kelly et al. ............... 211/60.1 |
| 6,048,503 A | | 4/2000 | Riley et al. |
| 6,059,111 A | | 5/2000 | Davila et al. |
| 6,161,695 A | * | 12/2000 | Nicolais ............... 206/438 |
| 6,164,044 A | * | 12/2000 | Porfano et al. ............... 53/471 |
| 6,189,292 B1 | * | 2/2001 | Odell et al. ............... 53/425 |
| 6,286,678 B1 | * | 9/2001 | Petrek ............... 206/443 |
| 6,412,639 B1 | | 7/2002 | Hickey |
| 6,534,015 B1 | * | 3/2003 | Viot et al. ............... 422/564 |
| 6,588,594 B2 | | 7/2003 | Andersen et al. |
| 6,715,264 B2 | | 4/2004 | Liakopoulos et al. |
| 7,100,768 B2 | * | 9/2006 | Grimard et al. ............... 206/438 |
| 7,169,361 B2 | * | 1/2007 | Arnold et al. ............... 422/526 |
| 7,232,038 B2 | | 6/2007 | Whitney |
| 7,428,807 B2 | | 9/2008 | Vander Bush et al. |
| 2003/0182900 A1 | | 10/2003 | Bowden et al. |
| 2003/0206825 A1 | | 11/2003 | Vellutato |
| 2004/0187438 A1 | | 9/2004 | Clarke et al. |
| 2006/0016156 A1 | | 1/2006 | Bush et al. |
| 2007/0034547 A1 | | 2/2007 | Strona |
| 2009/0100802 A1 | | 4/2009 | Bush et al. |

FOREIGN PATENT DOCUMENTS

| | | |
|---|---|---|
| JP | 200219726 A | 1/2002 |
| JP | 2002505921 T | 2/2002 |
| WO | 9425366 A1 | 11/1994 |

OTHER PUBLICATIONS

English Translation of Office Action issued May 26, 2009 from corresponding International Application No. MX/A/2007/000297.

Int'l Search Report issued on May 15, 2008 with Written Opinion Issued May 5, 2008 in Int'l Application No. PCT/US05/23138.

AU Search Report and Written Opinion issued Mar. 26, 2008 in SG Patent Application No. SG200609117-7.

Office Action issued Jul. 13, 2007 in U.S. Appl. No. 11/680,710.

Office Action issued Aug. 8, 2007 in U.S. Appl. No. 11/171,814.

Office Action issued Dec. 29, 2006 in U.S. Appl. No. 11/171,814.

Office Action issued May 17, 2007 in U.S. Appl. No. 11/171,814.

Office Action issued Oct. 18, 2006 in U.S. Appl. No. 11/171,814.

Response to Office Action dated Nov. 16, 2006 in U.S. Appl. No. 11/171,814.

Response to Office Action dated Mar. 28, 2007 in U.S. Appl. No. 11/171,814.

Response to Office Action and RCE Request dated Jul. 20, 2007 in U.S. Appl. No. 11/171,814.

Response to Office Action dated Sep. 25, 2007 in U.S. Appl. No. 11/680,710.

Office Action Issued Sep. 20, 2010 in CN Application No. 200580023330.1.

Office Action Issued on Sep. 13, 2010 in U.S. Appl. No. 12/346,139.

Office Action Issued Feb. 28, 2011 in JP Application Ser. No. 2007-519401.

Office Action Issued Mar. 23, 2011 in U.S. Appl. No. 12/346,139.

* cited by examiner

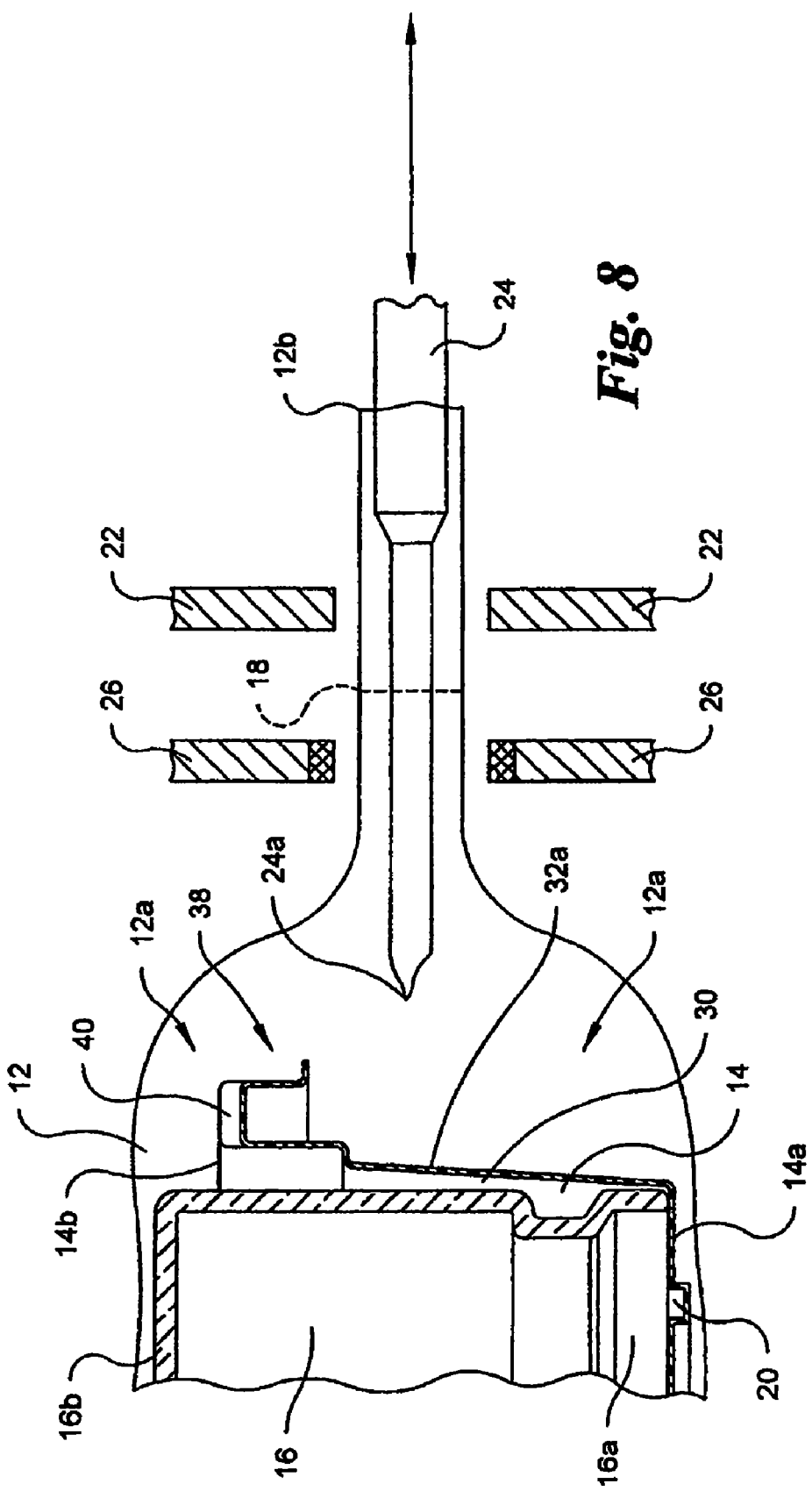

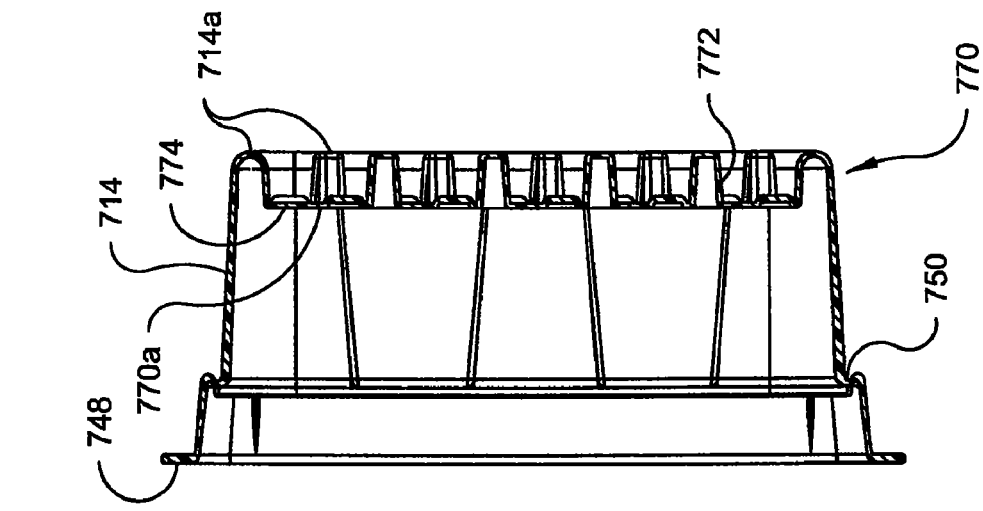
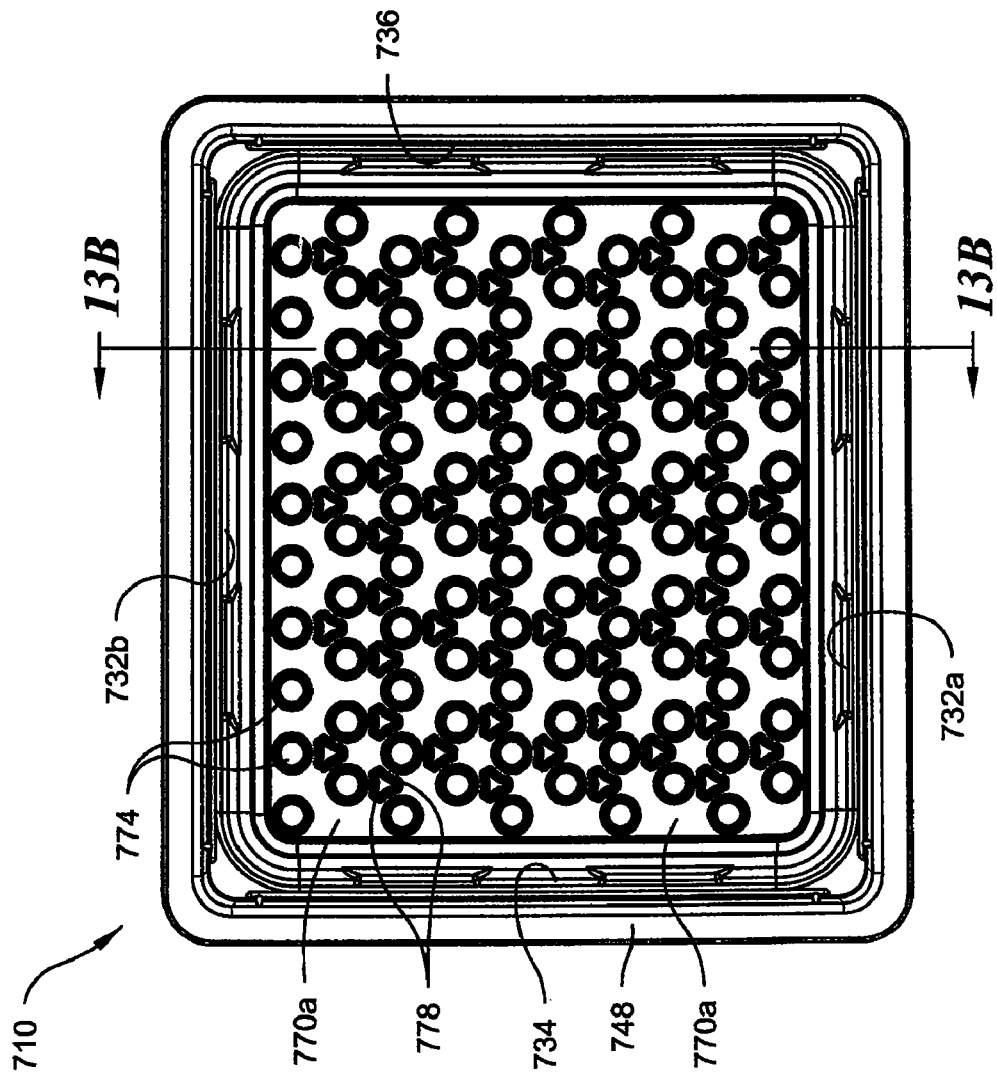
Fig. 13B
Fig. 13A

VACUUM PACKAGE SYSTEM

CROSS-REFERENCE TO RELATED APPLICATIONS

The present application is a continuation-in-part of pending U.S. patent application Ser. No. 12/346,139, filed Dec. 30, 2008 and entitled "Vacuum Package System," which is a continuation-in-part of U.S. patent application Ser. No. 11/171,814, filed Jun. 30, 2005 and entitled "Vacuum Packaging System and Method," now abandoned, which claims the benefit of U.S. Provisional Application No. 60/584,826, filed Jul. 1, 2004.

BACKGROUND OF THE INVENTION

The present invention relates broadly to vacuum packaging systems and, more particularly, to a vacuum packing system that protects and preserves sterilized medical containers during storage and/or shipment.

Medical containers generally must be sterile, have a low level of non-viable particulate matter and have a low or undetectable pyrogen level prior to the introduction of medication or another medical product into the medical container such that the product is not contaminated. One having ordinary skill in the art will realize that the medical containers are not necessarily completely sterile and free of all pyrogens prior to being filled with a medical product. However, the medical containers may be referred to as being sterile, pyrogen free and non-viable particulate matter free, meaning that the medical containers have a high sterility, a low or non-pyrogenic level and a low level of non-viable particulate matter. Common medical containers, for example, vials and syringes, are typically shipped from the vial or syringe molder in a permeable, non-sterile package and are sterilized, washed and depyrogenated to reduce pyrogen levels before introduction into a vial or syringe filling assembly line.

Glass vials and syringes may be washed and heated to a predetermined temperature for a predetermined time to eliminate non-viable particulate matter, reduce pyrogen levels and sterilize the vials and syringes. This process is relatively simple for a manufacturer who fills vials or syringes to perform because the glass vials and syringes are relatively easy to wash and place into a heated oven for the predetermined time. However, polymeric or plastic vials and syringes are typically unable to withstand the temperature required to reduce pyrogens to a non-pyrogenic level and sterilize the vials and syringes. The plastic vials and syringes may be washed and irradiated to reduce pyrogens and sterilize the vials and syringes, but the plastic vials and syringes are difficult to dry and the process is time consuming and generally will not result in removal of pyrogens to an acceptable level for filling. Accordingly, it would be advantageous to ship plastic vials and syringes directly from the vial and syringe molder that are sterile and pyrogen free during and after their shipment. Shipment of sterilized plastic vials and syringes to the assembly line would eliminate the extra sterilization, pyrogen reduction and non-viable particulate matter reduction processes that must be performed. In addition, vials and syringes are typically sterile, have a low pyrogen level and a low non-viable particulate matter level when they come out of a molding process and it would be advantageous to ship the vials and syringes in this condition without impacting their sterility, low pyrogen level and low non-viable particulate level.

Medical containers are typically shipped in boxes, trays or other like shipping containers that are permeable, not sterile and have a relatively high level of pyrogens. In addition, the shipping containers are often utilized to hold the medical containers in an orderly fashion in a clean room such that a robot is able to pick the medical containers out of the shipping containers and place them onto an assembly line. Accordingly, in order to enter the clean room environment, the shipping containers must also be sterile, have a low non-viable particulate matter level and have a low pyrogen level. Therefore, the shipping containers must also be sterilized, depyrogenated and cleaned of particulate matter before they enter the clean room. It would be advantageous to directly ship sterile, pyrogen free and non-viable particulate matter free medical containers in a sterilized, pyrogen free and non-viable particulate matter free container that may be taken directly to a clean room for filling of the medical containers.

Further, when medical containers are shipped in permeable boxes or trays in permeable bags, the vials and syringes may shift or vibrate during their shipment. When the vials and syringes shift and/or vibrate during transport, they may rub against each other causing surface damage and potentially introducing particulates into the bag and onto the vials and syringes. Accordingly, it would be advantageous to ship the vials and syringes in a package that generally does not permit significant shifting, movement or vibration of the vials and syringes, thereby resulting in reduced damage to the vials and syringes during shipping.

BRIEF SUMMARY OF THE INVENTION

Briefly stated, a preferred embodiment of the present invention is directed to a vacuum packaging system for transporting a plurality of medical containers. The vacuum packaging system includes a plurality of medical containers each including a head side and a base side and a tray that receives and supports the medical containers. The tray includes opposing first and second side walls, opposing side and rear walls and a bottom floor. The walls extend generally perpendicularly from the bottom floor of the tray to a top edge thereof. A nesting plate is removably mountable in the tray and includes a top surface, a bottom surface and a plurality of generally cylindrical sleeves. Each of the plurality of sleeves receiving one of the plurality of medical containers. A support surface within the tray generally extends parallel to and spaced a predetermined distance from the bottom floor of the tray and receives and supports the nesting plate. An air impervious flexible film defines an internal cavity. The air impervious flexible film completely surrounding the tray and the medical containers. The internal cavity being evacuated to and maintained at a predetermined vacuum level below atmospheric pressure.

In another aspect, a preferred embodiment of the present invention is directed to a vacuum packaging system for transporting a plurality of medical containers. The vacuum packaging system includes a plurality of medical containers each having a head side and a base side and a tray that receives and supports the medical containers. The tray includes a first and second side walls, opposing front and rear walls and a bottom floor. The walls extend generally perpendicularly from the bottom floor to a top edge of the tray. A support surface within the tray extends generally parallel to and spaced a predetermined distance from the bottom floor of the tray. The support surface having a plurality of spaced-apart support members extending generally perpendicularly from the floor of the tray and a lip extending around at least a portion of each of the walls of the tray. An air impervious flexible film defines an internal cavity. The air impervious flexible film completely surrounds the tray of the medical containers. The internal cavity is evacuated to and maintained at a predetermined vacuum level below atmospheric pressure.

BRIEF DESCRIPTION OF THE SEVERAL VIEWS OF THE DRAWINGS

The following detailed description of the preferred embodiments of the present invention will be better understood when read in conjunction with the appended drawings. For the purposes of illustrating the invention, there is shown in the drawings several embodiments which are presently preferred. It is understood, however, that the invention is not limited to the precise arrangements and instrumentalities shown. In the drawings:

FIG. 8 is a magnified cross-sectional, side elevational view of a vacuum probe partially positioned within the vacuum bag of the vacuum packaging system shown in FIG. 1;

FIG. 13A is a top plan view of a tray of a vacuum packaging system for holding a plurality of syringes mounted on a nesting plate in the tray that is positioned within a vacuum bag in accordance with an seventh preferred embodiment of the present invention;

FIG. 13B is a cross-sectional elevation view of the tray of the vacuum packaging system shown in FIG. 13A, taken along line 13B-13B of FIG. 13A;

DETAILED DESCRIPTION OF THE INVENTION

Figure 1:
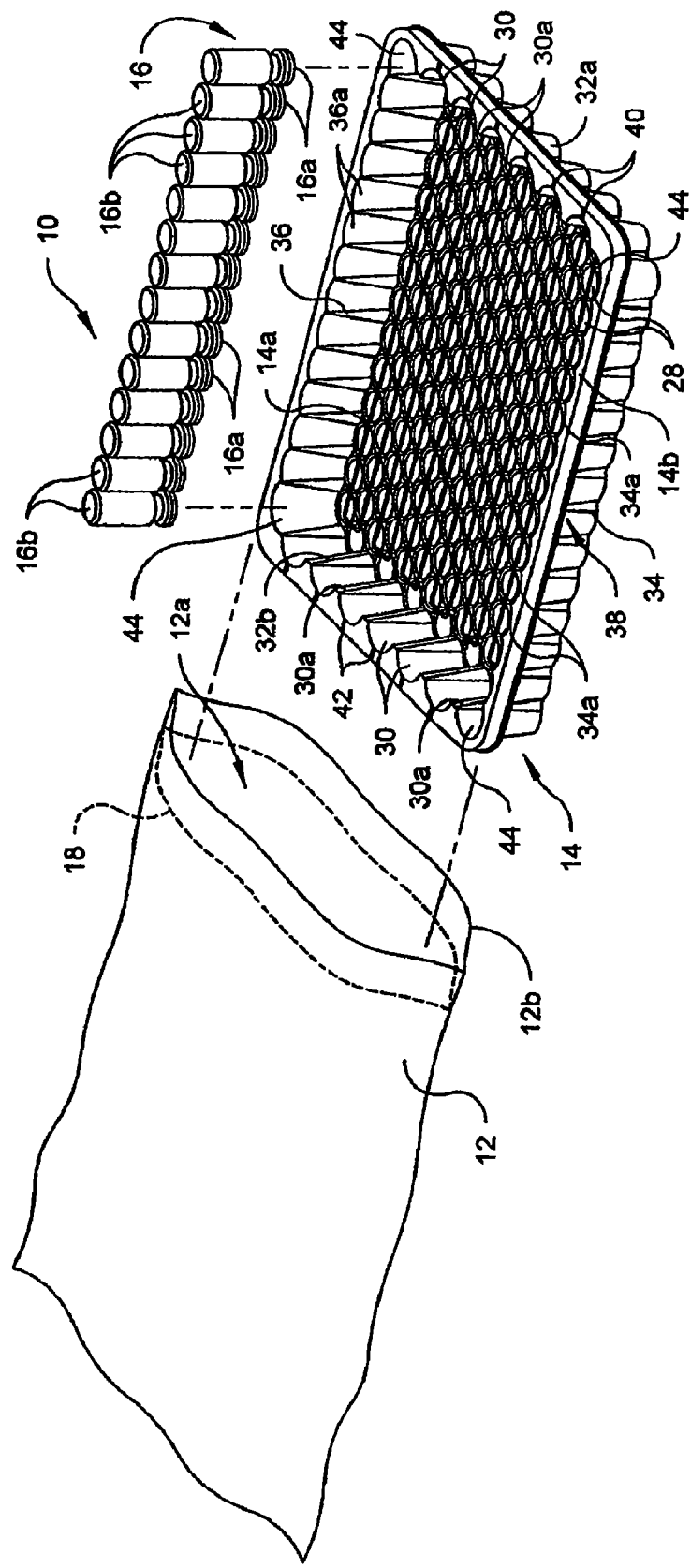
FIG. 1 is an exploded view of a vacuum packaging system including a tray, a row of vials and a vacuum bag in accordance with a first preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the vacuum package system and designated parts thereof. The terminology includes the words specifically mentioned, derivatives thereof and words of similar import. Additionally, the word "a" as used in the specification means "at least one."

Referring to the drawings in detail, wherein like numerals indicate like elements throughout, there is shown in FIGS. 1-5 and 8 a first preferred embodiment of a vacuum packaging system, generally designated 10, for transporting a plurality of medical containers 16. The vacuum packaging system 10 includes an air impervious film 12, a tray 14 and the plurality of medical containers 16. In the first preferred embodiment, the medical containers 16 are preferably comprised of vials 16 and the air impervious film 12 is preferably comprised of a vacuum bag 12 having an internal cavity 12a. The medical containers 16 are not limited to vials 16 and the air impervious film 12 is not limited to a vacuum bag 12. For example, the medical containers 16 may be comprised of nearly any container or vessel that is transported from a medical container manufacturer to an end user. In addition, the air impervious film 12 may be comprised of a film or sheet of material that is formed into a container or bag having a cavity into which the tray 14 may be inserted. The plurality of vials 16 are preferably stackable in the tray 14 and the vacuum bag 12 is preferably large enough to hold the tray 14 with the plurality of vials 16 stacked therein.

The tray 14 supports the vials 16 in the first preferred embodiment and the air impervious film 12 defines the internal cavity 12a. In an assembled configuration, the air impervious flexible film 12 completely surrounds the tray 14 and the medical containers 16 and the internal cavity 12a is evacuated to a predetermined vacuum level below atmospheric pressure. When the internal cavity 12a is evacuated, the air impervious flexible film 12 is preferably in facing engagement with at least portions of the vials 16 and the tray 14, thereby holding the vials 16 in a relatively fixed position in the tray 14 such that the vials 16 generally do not move during transportation. Specifically, it is preferred that the tray 14 and air impervious film 12 hold the vials 16 in a manner that generally prevents significant movement of the vials 16 such that the vials 16 generally do not rub against each other during shipping, as will be described in greater detail below In the first preferred embodiment, the vials 16 are constructed of a polymeric or, preferably, a plastic material and have a shape of a conventional vial that typically holds medication, another liquid substance, a powdered medical product or another like product. The vials 16 are not limited to plastic constructions and may be constructed of nearly any material that may be formed into the general shape of the vials 16, perform the typical functions of the vials 16 and withstand the normal operating conditions of the vials 16. For example, the vials 16 may be constructed of nearly any polymeric or glass material. However, the plastic material is preferred for construction of the vials 16 because of the ease of moldability of the plastic material and the generally high resistance to breakage if dropped or impacted by an external force. The plastic material also provides surfaces that are receptive to sterilization and pyrogen elimination.

In the first preferred embodiment, the tray 14 is constructed of a thermoformed polymeric material. The tray 14 is not limited to being thermoformed and may be constructed using nearly any manufacturing process that is able to form the general shape and size of the tray 14, such as injection molding, machining or another like manufacturing process. In the preferred embodiment, the tray 14 is constructed of a thermoformed plastic material that has a shape and size that accommodates stacking and storage of the plurality of vials 16. The thermoformed plastic material is preferred because of its formability, ability to be sterilized and relatively low cost. The tray 14 and vacuum bag 12 are also preferably transparent or semi-transparent so that a user is able to perform a visual inspection of the vials 16 stacked in the tray 14 in the assembled configuration or at any time the vials 16 are stacked in the tray 14, but are not so limited. The vacuum bag 12 and tray 14 may also be constructed of a semi-transparent or opaque material.

Referring to FIGS. 1-5, in the first preferred embodiment, the tray 14 includes opposing first and second sidewalls 32a, 32b and opposing front and rear walls 34, 36. In the first preferred embodiment, the tray 14 has a generally square or rectangular-shape with the walls 32a, 32b, 34, 36 separated from each other by a floor 14a. The preferred walls 32a, 32b, 34, 36 extend from the floor 14a to a top edge 14b. In the first preferred embodiment, the tray 14 has a tray height $H_w$ of approximately one and seven-eights inches (1⅞"). The tray height $H_w$ is not limited to the above-listed height and may have nearly any height that is able to accommodate the containment of nearly any sized and shaped medical container 16. The one and seven-eights inch tray height $H_w$ for the walls 32a, 32b, 34, 36 is preferred for packaging and transporting the preferred vials 16 in the tray 14.

Referring to FIGS. 1-4, in the first preferred embodiment, side pockets 30 are formed in the first and second sidewalls 32a, 32b. The side pockets 30 are preferably arc-shaped depressions formed in the first and second sidewalls 32a, 32b that extend outwardly relative to a center of the tray 14 and conform to at least a portion of an external surface of one of the medical containers 16 or vials 16 when the vials 16 are located in the tray 14 proximate one of the side pockets 30. Preferably, the sidewalls 32a, 32b conform to at least a portion of an external surface of only one of the medical containers 16 when the medical containers 16 are located in the tray proximate one of the side pockets.

In the first preferred embodiment, each of the first and second sidewalls 32a, 32b include six (6) side pockets 30 to accommodate twelve (12) staggered rows of medical containers or vials 16. The side pockets 30 preferably conform to at least a portion of the external surface of the vials 16 to provide stability for each row of vials 16 within the tray 14 to generally prevent the row of vials 16 from toppling or falling over. Side peaks 30a are also defined between each of the side pockets 30 and conform to a relatively smaller portion of the external surface of at least one medical container or vial 16. The peaks 30a in concert with an opposing side pocket 30 formed on an opposite sidewall 32a, 32b provide additional stability for the row of vials 16. The tray 14 is not limited to the inclusion of the arc-shaped side pockets 30 and the peaks 30a that generally conform to a portion of the external surface of the vials 16. For example, the sidewalls 32a, 32b may have a generally planar internal surface or may have a flexible surface that is able to flex to conform to a portion of the external shape of the containers 16. In addition, the tray 14 is not limited to the above-listed number of pockets 30 and peaks 30a on the sidewalls 32a, 32b and may include nearly any number of side pockets 30 and peaks 30a to accommodate nearly any number of containers 16. However, the side pockets 30 and peaks 30a are preferred in the sidewalls 32a, 32b to provide stability for the vials 16 when they are stacked in the tray 14.

In the first preferred embodiment, the tray 14 also includes front pockets 34a in the front wall 34 and rear pockets 36a in the rear wall 36. The front and rear pockets 34a, 36a preferably conform to at least a portion of the external surface of one of the medical containers or vials 16 when the containers 16 are located in the tray 14 proximate one of the front and rear pockets 34a, 36a. In the first preferred embodiment, the front and rear walls, 34, 36 each include twelve opposing front and rear pockets 34a, 36a to accommodate twelve columns of vials 16 in the tray 14. The tray 14 is not limited to the inclusion of twelve front and rear pockets 34a, 36a on the front and rear walls 34, 36 nor to the inclusion of any front and rear pockets 34a, 36a. For example, the tray 14 may include nearly any number of front and rear pockets 34a, 36a that provide stability for the vials 16 when they are mounted or inserted into the tray 14 or may include no front and rear pockets 34a, 36a such that the vials 16 simply rest against a planar front and/or rear wall 34, 36. However, the front and rear pockets 34a, 36a are preferred to provide stability for the vials 16 when they are placed into the tray 14.

Figure 3:
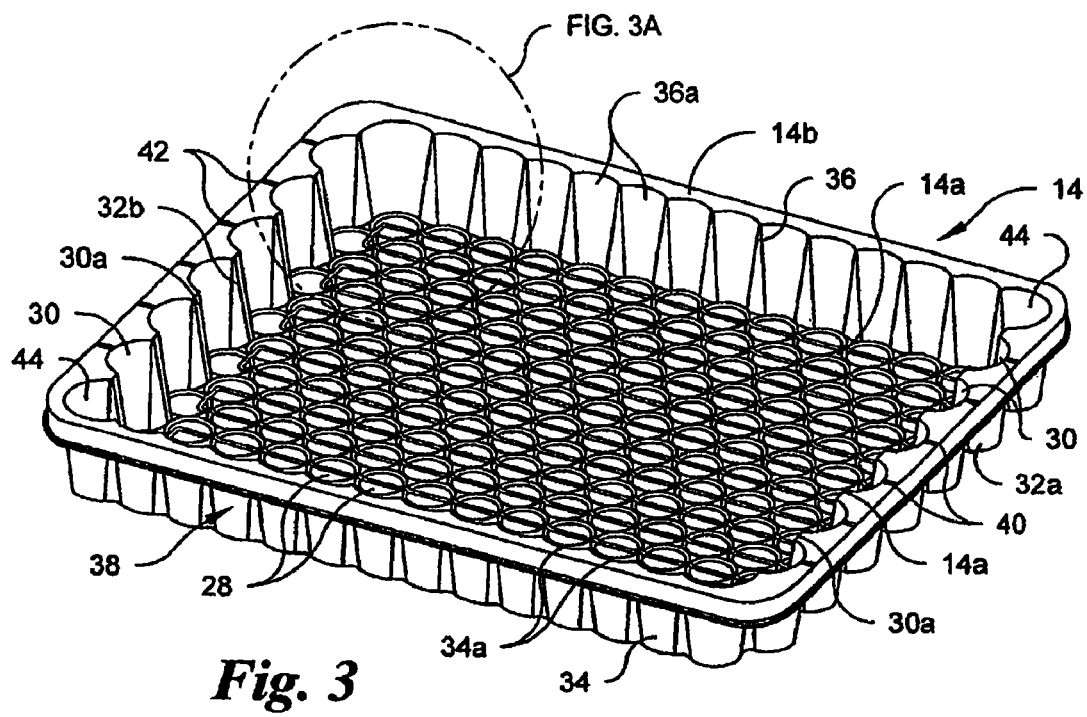
FIG. 3 is a top perspective view of the tray of the vacuum packaging system shown in FIG. 1.
Figure 4:
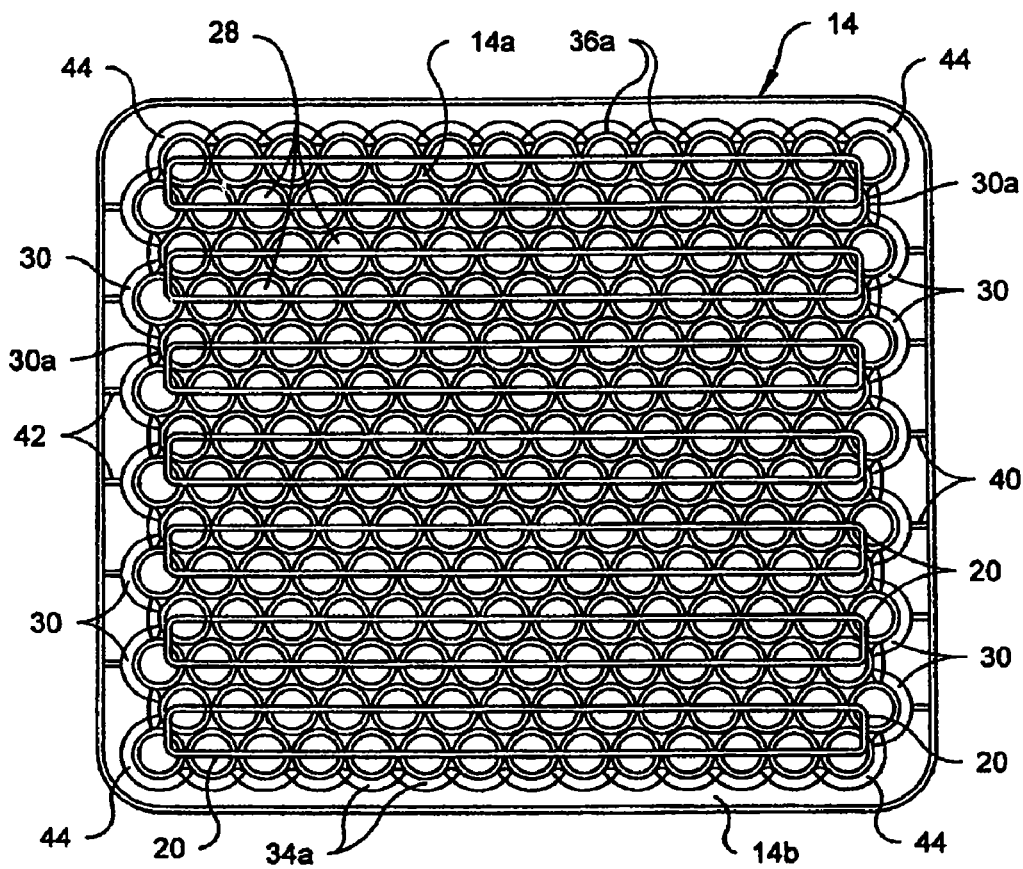
FIG. 4 is a top plan view of the tray of the vacuum packaging system shown in FIG. 1.

Referring to FIGS. 1 and 3-4, in the first preferred embodiment, the tray 14 includes corner pockets 44 at the intersection of the first and second sidewalls 32a, 32b and the front and rear walls 34, 36, respectively. The corner pockets 44 preferably conform to and are in engagement with at least a portion of the external surface of the medical containers 16 that are positioned in corners of the tray 14. Similar to the side pockets 30 and front and rear pockets 34a, 36a, the corner pockets 44 stabilize the rows and columns of medical containers 16 that are positioned in the tray 14. The tray 14 is not limited to the inclusion of the corner pockets 44 and may include corner pockets having nearly any size or shape to accommodate nearly any sized or shaped medical container 16 or may have a generally squared corner. The corner pockets 44 preferably have a generally arcuate shape to accommodate the generally cylindrical vials 16 that are mounted in the tray 14.

Referring to FIGS. 1-4, the tray 14 includes the floor 14a and the top edge 14b opposite the floor 14a with the sidewalls 32a, 32b and front and rear walls 34, 36 therebetween. The plurality of vials 16 is preferably stacked in the tray 14 with a head side 16a in contact with the floor 14a and a base side 16b proximate the top edge 14b. The vials 16 are preferably loaded into the tray 14 in this orientation, typically to accommodate loading of the vials 16 into an assembly line by an operator. Alternatively, the vials 16 may be stacked in the tray 14 with the base side 16b in contact with the floor 14a and the head side 16a adjacent the top edge 14b, typically to accommodate loading of the vials into the assembly line by a robot. In addition, the vials 16 may be loaded or positioned in the tray 14 such that their sides are in contact with the floor 14a. One having ordinary skill in the art will realize that the vials 16 are not limited to being stacked in the tray 14 in the above-described orientations and may be stacked in nearly any orientation for insertion into the vacuum bag 14. The plurality of vials 16 are preferably stacked relatively tightly in the tray 14 to reduce movement of the vials 16 relative to each other and the tray 14 during movement or shipping of the tray 14.

Referring to FIGS. 1 and 3-4, in the first preferred embodiment, the tray 14 also includes depressions 28 formed in the floor 14a of the tray 14. The depressions 28 preferably conform to the head side 16a and/or base side 16b of the medical container 16 when the containers 16 are positioned in the tray 14 to orient the medical container 16 with respect to the tray 14. The tray 14 preferably includes a plurality of depressions 28, wherein each depression 28 conforms to a single head or base 16a, 16b of a single container or vial 16. In the first preferred embodiment, one hundred ninety-six (196) depressions are formed in the floor 14a to accommodate one hundred ninety-six vials 16 that are positioned within the preferred tray 14. The tray 14 is not limited to inclusion of one hundred ninety-six depressions and may include nearly any number of depressions 28 to accommodate nearly any number of vials or medical containers 16 within the tray 14. In addition, the tray 14 is not limited to the inclusion of depressions 28 and may have a generally planar floor 14 to support the vials 16. The depressions 28 preferably aid in properly orienting the vials 16 within the tray 14.

Figure 3A:
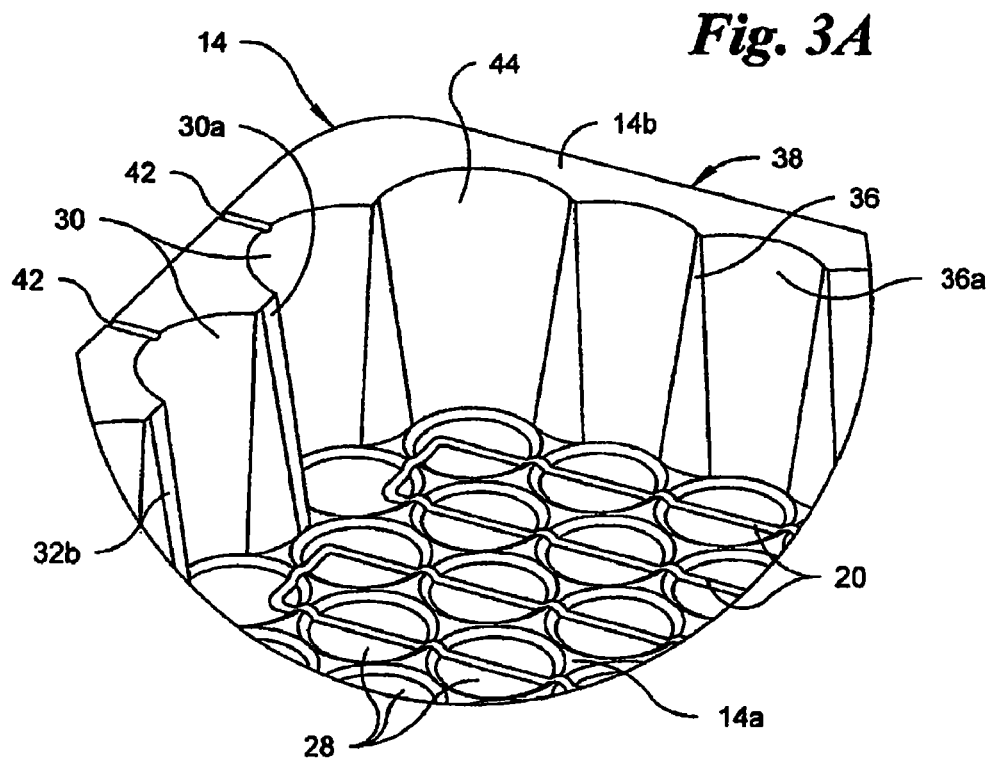
FIG. 3A is magnified, partial top perspective view of the tray of the vacuum packaging system shown in FIG. 1, taken from within the dashed circle of FIG. 3.

Referring to FIGS. 3, 3A and 8, in the first preferred embodiment, the tray 14 includes a U-shaped peripheral flange 38 formed proximate a mouth of the tray 14. The top edge 14b forms a bottom of the U-shape of the peripheral flange 38 in the first preferred embodiment. The U-shaped peripheral flange 38 provides strength and stiffness to the tray 14 to resist crushing or other failure of the mouth of the tray 14 under loading. For example, the peripheral flange 38 preferably provides strength and stiffness to the tray 14 such that the top edge 14b generally does not deform significantly or buckle when the tray 14 filled with vials 16 is positioned in the internal cavity 12a, a vacuum is drawn from the internal cavity 12a and the bag 12 is sealed. The tray 14 is not limited to the inclusion of the U-shaped peripheral flange 38 and may include nearly any sized and shaped top edge 14b that is able to perform the general functions of the tray 14 and withstand the normal operating conditions of the tray 14. The preferred peripheral flange 38 is integrally molded with the tray 14 but is not so limited and may be comprised of a separate component that is mounted to the tray 14 after construction of the tray 14. Alternatively, the top edge 14b may be rolled or have an increased thickness when compared to the walls 32a, 32b, 34, 36 of the tray 14 to provide stiffness and strength at the top edge 14b. The tray 14 is not limited to the inclusion of the U-shaped peripheral flange 38 and may include a terminal end at the top of the walls 32a, 32b, 34, 36 without stiffening or reinforcement.

Referring to FIGS. 1-4 and 8, in the first preferred embodiment, vents are formed in the peripheral flange 38 and are comprised of a first series of troughs 40 formed in the top edge 14b of the peripheral flange 38 proximate the first sidewall 32a and a second series of troughs 42 formed in the top edge 14b of the peripheral flange 38 proximate the second sidewall 32b. The first and second series of troughs 40, 42 are preferably integrally molded into the peripheral flange 38 at the top edge 14b as arc-shaped cavities. In the first preferred embodiment, each trough 40, 42 is associated with one of the side pockets 30 in the first and second sidewalls 32a, 32b. Accordingly, in the first preferred embodiment, the first sidewall 32a includes six troughs 40 and the second sidewall 32b includes six additional troughs 42. The troughs 40, 42 preferably permit the flow of air or purge gas from or into the tray 14 when a vacuum is drawn or purge gas flows into the internal cavity 12a and the tray 14 is in the internal cavity 12a, as will be described in greater detail below. The tray 14 is not limited to the inclusion of the first and second series of troughs 40, 42 or to the above-described number of troughs 40, 42 in the peripheral flange 38. For example, the vents may be comprised of a plurality of holes in one of the first or second sidewalls 32a, 32b or the front and rear walls 34, 36 or a single or multiple holes formed in the floor 14a of the tray 14. The vents are preferably formed in the tray 14 such that air and/or purge gas may flow out of the tray 14 when a vacuum is drawn from the internal cavity 12a and the tray 14 is in the internal cavity 12a, as will be understood by one having ordinary skill in the art, to permit air and/or purge gas to flow into and out of the tray 14 without being blocked by the flexible film 12.

Referring to FIGS. 3-4 and 8, in the first preferred embodiment, the tray 14 also includes at least one vacuum groove 20 formed in the floor 14a. The vacuum groove 20 is preferably comprised of a channel that traverses the floor 14a and is in contact with each one of the plurality of depressions 28. The vacuum groove 20, similar to the vents, provides a conduit for the release of air and/or purge gas from the medical containers 16 that are positioned in the tray 14 when a vacuum is drawn from the internal cavity 12a. The vacuum groove 20 preferably permits the release of gas or air from the inside of the vials 16 such that air is typically not trapped within the vials 16 when the vacuum is drawn from the internal cavity 12a or purge gas is introduced into the internal cavity 12a. The tray 14 is not limited to the inclusion of the vacuum groove 20 and may not include a vacuum groove 20 or the tray 14 may be include a mound or mounds of material that orient the medical containers 16 such that gas is able to escape from the inside of the containers 16 by providing a gap between at least a portion of the head side 16a relative to the floor 14a when the medical container 16 are positioned in the tray 14. In addition, the vacuum groove 20 may be comprised of individual holes located in the depressions 28 to allow the release of air from inside the containers 16 when a vacuum is drawn from the internal cavity 12a.

Figure 5:
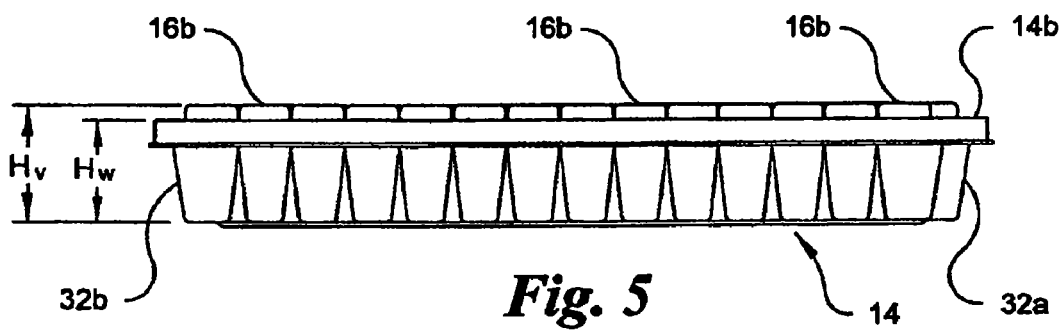
FIG. 5 is a front elevational view of the tray and rows of vials stacked in the tray of the vacuum packaging system shown in FIG. 1.

Referring to FIGS. 5 and 8, in the first preferred embodiment, the base ends 16b of the vials 16 protrude from and above the top edge 14b of the tray 14 when the vials 16 are mounted or stacked in the tray 14. In the first preferred embodiment, the vials 16 have a vial height $H_V$ of approximately two and one-eighth inches (2⅛") resulting in the base ends 16b of the vials 16 protruding from the top edge 14b approximately one-quarter inch (¼"). The vials 16 are not limited to having a vial height $H_V$ of two and one-eighth inches and may have nearly any height that may be accommodated by the tray 14. In addition, the vials 16 are not limited to protruding from the top edge 14b of the tray 14 and may be positioned in the tray 14 such that their base or head ends 16b, 16a are flush with the top edge 14b or are recessed from the top edge 14b. However, it is preferred that the vials 16 protrude from the top edge 14b such that the vacuum bag 12 engages portions of the head end 16a or base end 16b and sides of the vials 16 when the vacuum is drawn from the internal cavity 12a to securely hold the vials 16 in position in the tray 14.

Figure 2:
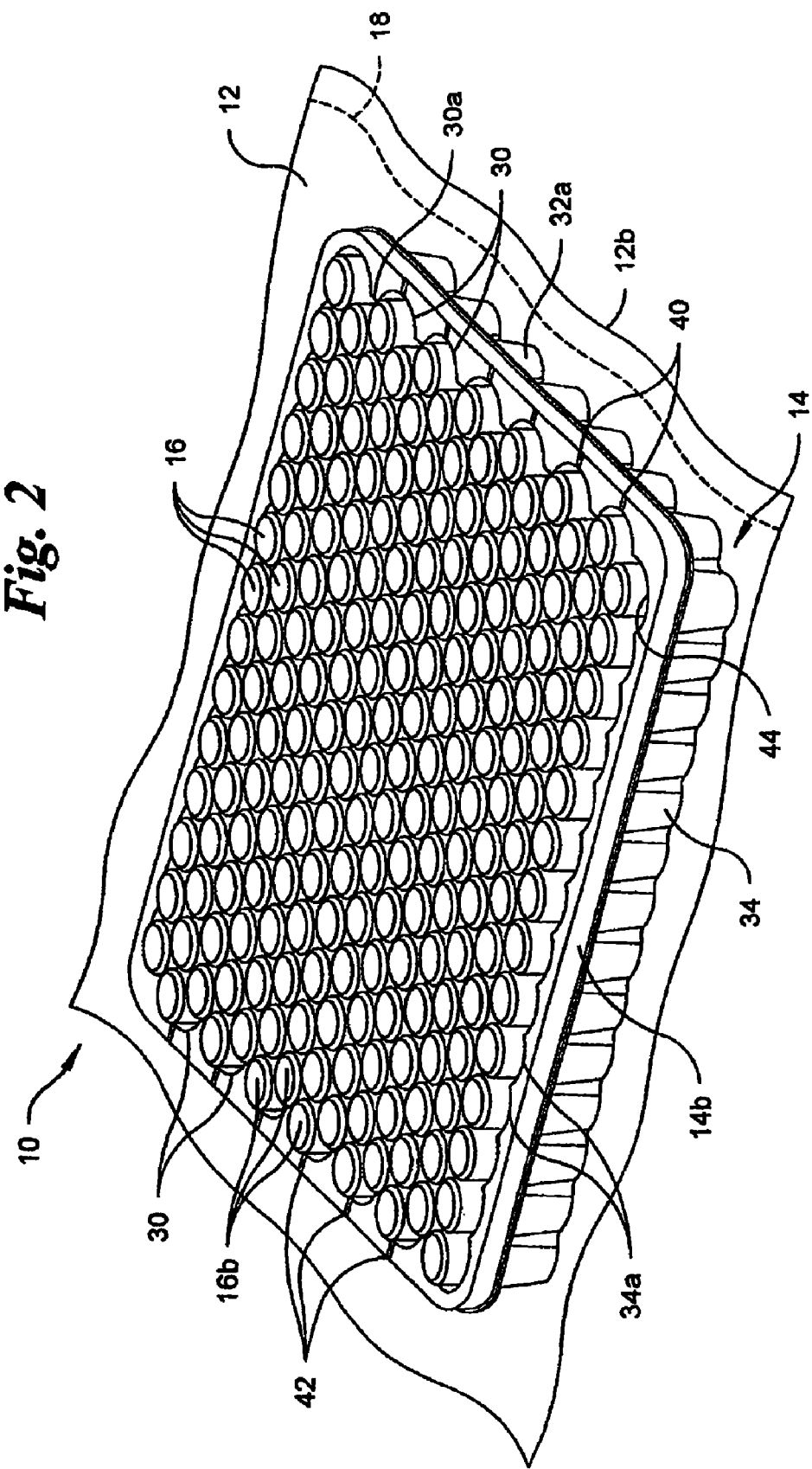
FIG. 2 is a top perspective view of the tray with the vials stacked therein and the tray positioned in the vacuum bag of the vacuum packaging system shown in FIG. 1.

Referring to FIGS. 1, 2 and 8, in the first preferred embodiment, the flexible film 12 is comprised of the vacuum bag 12 having the general shape of a rectangular bag with an open end 12b and the internal cavity 12a. The internal cavity 12a is preferably large enough to encompass the tray 14 when it is filled with the stacked plurality of vials 16. The vacuum bag 12 is preferably constructed of a multi-layer polymer that is resistant to gas permeation, but is not so limited. The vacuum bag 12 is also preferably constructed of a material that is able to be sterilized, depyrogenated, cleaned of non-viable particulate matter and sealed at its open end 12b such that gas does not permeate through the seal. Many types and sizes of vacuum bagging material may be utilized to construct the vacuum bag 12, as will be understood by one having ordinary skill in the art.

The vacuum bag 12 of the preferred embodiments includes a tear notch 18 (FIG. 2) that accommodates opening of the vacuum bag 12 after it has been positioned around the tray 14 and vials 16, evacuated and sealed. The tear notch 18 simplifies opening of the vacuum packaging system 10 to permit an end user to access the tray 14 and vials 16. One having ordinary skill in the art will realize that the notch 18 is provided for opening convenience and is not required for the operation of the vacuum packaging system 10. The tear notch 18 is preferably an initiation notch that provides a sharp notch to begin a tear to open the vacuum bag 12, but may be constructed of a low strength line or partially perforated line in the vacuum bag 12 that provides an area to tear open the sealed vacuum bag 12. The preferred vacuum bag material is oriented such that the tear will proceed from the tear notch 18 along a line generally perpendicular to a side edge of the vacuum bag 12. Vacuum bag materials having this characteristic are known to those having skill in the vacuum bag art. The vacuum bag 12 may not include the tear notch 18 and would continue to function, as would be understood by one having ordinary skill in the art.

In operation, in the first preferred embodiment, the medical containers or vials 16 are molded and at the conclusion of the molding operation, the vials 16 are relatively pyrogen free and non-viable particulate matter free. The vials 16 are inserted into the tray 14 in this condition, preferably such that at least a portion of the vials 16 and most preferably such that the base end 16b extends above the top edge 14b. The tray 14 is also preferably sterile, pyrogen free and non-viable particulate matter free when the vials 16 are inserted therein. The tray 14 is inserted into the internal cavity 12a and the internal cavity 12a is evacuated to a predetermined vacuum pressure such that the flexible film 12 surrounds and engages the tray 14 and at least portions of the medical containers 16. Specifically, the flexible film 12 preferably engages the base ends 16b of the vials 16 and portions of the side surfaces, which extend out of the mouth of the tray 14 and exposed surfaces of the tray 14 under the force of external air pressure. The flexible film 12 is then sealed such that the predetermined vacuum pressure is generally maintained in the internal cavity 12a. The sealed flexible film 12 with the tray 14 and plurality of vials 16 therein may be transported without significant movement of the vials 16 because the atmospheric pressure on the flexible film 12 consolidates and holds the vials 16 in position in the tray 14. Accordingly, the vials 16 generally do not move during shipment, reducing the likelihood that the vials 16 rub up against each other and potentially damage each other. In addition, if the vials 16 and tray 14 are sterilized, non-viable particulate matter free and pyrogen free when they are inserted into the internal cavity 12a, the vials 16 and tray 14 are also generally in the same condition when the vacuum bag 12 is opened, assuming the predetermined vacuum pressure is retained in the internal cavity 12a.

In the first preferred embodiment, the vials 16 are inserted into the tray 14 by grasping one or more of the vials 16 with a mechanical or robotic arm (not shown) as the vials 16 flow off of a medical container molding assembly line. The mechanical arm is preferably associated with a robot that is able to place the vial 16 or a plurality of vials 16 into the tray 14 such that the vials 16 are positioned in rows within the tray 14 and each vial 16 is associated with a specific depression 28. Specifically, once the medical containers or vials 16 are molded by the medical container molder, the containers 16 are preferably handled exclusively by robots to limit exposure of the containers 16 to contaminants or pyrogens before they are filled with a medical product. Prior to inserting the container 16 into the tray 14, the container 16 is preferably robotically transported to an inspection station for dimensional and quality inspection. Inspection preferably determines whether the container 16 has an acceptable dimensional shape because improperly sized and/or shaped containers 16 may not properly stack within the tray 14 and may be unusable by a customer. The containers 16 are preferably positioned in the tray 14 such that their head sides 16a are in facing engagement with the depressions 28 and their base sides 16b protrude above the top edge 14b of the tray 14.

In the first preferred embodiment, the vials 16 are robotically inserted into the tray 14 in a series of fourteen (14) rows between the first and second sidewalls 32a, 32b. The first row of vials 16 preferably includes fourteen vials 16 that are associated with individual depressions 28 proximate the front or rear walls 34, 36. The end vials 16 in the rows are mounted such that they are within or conform to the shape of the corner pockets 44 and the twelve vials 16 in the middle of the row are associated with the front or rear pockets 34a, 36a on the front or rear walls 34, 36. A second row of vials 16 is then inserted into the tray 14 immediately adjacent the first row with one of the end vials 16 associated with one of the side pockets 30 and an opposing vial 16 on an opposite end of the row associated with one of the peaks 30a. Each of the vials 16 in the second row is also associated with a depression 28. The additional rows of vials 16 are similarly inserted into the tray 14 until the tray 16 is completely filled with vials or other medical containers 16. The vials 16 are not limited to being inserted into the tray 14 in rows and may be individually inserted into the tray 14 in a random pattern or may all be inserted into the tray 14 at one time. However, it is preferred that the vials 16 are positioned or stacked in the tray 14 in the manner shown in FIG. 2 such that the vials 16 are closely stacked in the tray 14 to generally prevent significant movement of the vials 16 during movement or shipping.

Referring to FIGS. 1, 2 and 8, as was described above, after the vials 16 are positioned in the tray 14, the tray 14 is inserted into the internal cavity 12a of the flexible film or vacuum bag 12. As was also described above, the vials 16 are preferably relatively pyrogen free and non-viable particulate matter free when they are positioned in the tray 14 and inserted in the internal cavity 12a. A vacuum probe 24 is inserted into the open end 12b such that a tip 24a of the probe 24 is in communication with the internal cavity 12a. A purge gas is introduced into the internal cavity 12a by the vacuum probe 24 and air is forced out of the internal cavity 12a. Sealing jaws 26 engage the open end 12b of the vacuum bag 12 such that additional air or purge gas generally does not escape or enter the internal cavity 12a through the open end 12b. The vacuum probe 24 is then actuated to draw a vacuum in the internal cavity 12a, thereby drawing the purge gas and air out of the internal cavity 12a such that the pressure within the internal cavity 12a is reduced to a predetermined vacuum pressure. As the vacuum is drawn from the internal cavity 12a, external air pressure urges the flexible film or vacuum bag 12 against the tray 14 and the vials 16. As the external pressure becomes higher, the vacuum bag 12 adheres relatively tightly to surfaces of the tray 14, preferably preventing movement of the vials 16 relative to the tray 14 or each other. The first and second series of troughs 40, 42 provide a conduit for air to escape the inside of the tray 14 as the film or bag 12 tightly adheres to the surfaces of the tray 14 such that additional vacuum can be drawn because the flexible film or bag 12 generally bridges over the troughs 32a, 32b providing a flow channel for the purge gas and air to escape from the internal cavity 12a. In addition, the vacuum groove 20 permits purge gas and/or remaining air to escape from inside the individual vials 16 because the head side 16a of the vial 16 is not in complete facing engagement with or sealed to the floor 14a of the tray 14. For example, if the floor 14 were flush, the head side 16a of the vial 16 may completely engage and create a seal with the planar floor 14a. If the head side 16a of the vial 16 is sealed, purge gas and air may be sealed within the vial 16 because no gap or conduit is provided for the escape of gas from the vial 16 and this gas may subsequently escape from the vial 16, potentially compromising the vacuum in the bag 12.

After the vacuum has been drawn in the internal cavity 12a to a predetermined level, sealing jaws 26 engage the flexible film or vacuum bag 12 proximate the open end 12b and preferably heat seal the vacuum bag 12 to maintain the vacuum within the internal cavity 12a. Because the predetermined vacuum is maintained in the internal cavity 12a, the vacuum bag 12 continues to adhere to the tray 14 and portions of the vials 16 to consolidate and hold the vials 16 in the tray 14, generally to prevent significant movement of the vials 16 relative to the tray 14 and rubbing of the vials 16 against each other. The vacuum probe 24 is removed from the internal cavity 12a and the vacuum bag 12 is also sealed at the entrance for the vacuum probe 24. The clamp jaws 22 and sealing jaws 26 release the vacuum bag 12 and the vacuum bag 12 is inspected to check for any leaks in the bag 12. If leaks are detected, the vacuum bag 12 may be repaired or discarded and the tray 14 may be inserted into another vacuum bag 12. If the predetermined vacuum pressure is maintained in the internal cavity 12a, the vials 16 generally maintain their sterile, pyrogen free and non-viable particulate matter free condition and do not significantly move or rub against each other during shipping or other movement because of the tight adherence of the vacuum bag 12 to the external surfaces of the vials 16 and tray 14.

Referring to FIG. 2, in the first preferred embodiment, the sealed vacuum bag 12 with the tray 14 and plurality of vials 16 are preferably irradiated to sterilize the bag 12, tray 14 and vials 16. The bag 12, tray 14 and vials 16 are preferably irradiated for sterilization because the material of the polymeric materials of the bag 12, tray 14 and vials 16 is typically unable to withstand high temperatures that would be required to bake or otherwise heat the bag 12, vials 16 and tray 14 to remove pyrogens and sterilize. Irradiation of the sealed bag 12, tray 14 and vials 16 is not limited and this step may be completely eliminated from the process if the vials 16, tray 14 and bag 12 are otherwise conditioned for sterilization prior to being inserted into the bag 12.

Referring to FIGS. 1 and 2, in the first preferred embodiment, the sealed and evacuated vacuum bag 12 with the sterile, pyrogen free and non-viable particulate matter free tray 14 and plurality of vials 16 mounted therein is preferably transported to a medical container filler such that the vials 16 can be filled with some type of fluid, preferably medication, saline or another medical product. Often, the assembly is transported as air cargo and is subjected to the reduced air pressure that is common during air travel. Accordingly, the predetermined vacuum within the vacuum bag 12 is preferably near or below the reduced pressure that is typically encountered during air travel. If the vacuum pressure in the bag 12 is not below this pressure, the consolidation of the vials 16 may be at least partially compromised by the bag 12 releasing from some surfaces of the tray 14 and vials 16, permitting the vials 16 and/or tray 14 to move within the bag 12. If the vacuum bag 12 releases from the tray 14 and vials 16, the vials 16 may move within the tray 14 and rub against each other, potentially damaging the vials 16. When the vacuum packaging assembly arrives at its destination, the vacuum bag 12 is preferably inspected to ensure that the bag 12 is engaged with the tray 14 and at least portions of the vial 16 indicating that the predetermined vacuum pressure within the internal cavity 12a has been maintained during shipping. Assuming the inspection reveals that the predetermined vacuum pressure has been maintained within the vacuum bag 12, the vacuum bag 12 is opened to gain access to the tray 14 and medical containers 16. The tray 14 is removed from the internal cavity 12a and the medical containers or vials 16 are removed from the tray 14, preferably robotically, for introduction onto an assembly line for filling the vials 16. If the predetermined pressure is maintained within the internal cavity 12a, medical products may be inserted into the vials 16 under the general assurance that the vials 16 and tray 14 are sterile, non-viable particulate matter free and pyrogen free. However, if the predetermined pressure is not maintained in the internal cavity 12a, the inspection typically reveals a breach in the bag 12, which may result in a necessity to sterilize, remove non-viable particulate matter and/or remove pyrogens from the vials 16 and tray 14 before introducing the tray 14 and/or vials 16 to a clean room environment or otherwise filling the vials 16 with medical products.

In the first preferred embodiment, the vacuum bag 12 preferably includes the tear notch or tear perforation 18 proximate the open end 12b. The tear notch or perforation 18 may be utilized to tear open the vacuum bag 12 to gain access to the tray 14 and vials 16. The vacuum bag 12 is not limited to the inclusion of the tear notch and/or tear perforation 18 and may include nearly any line of weakness or stress riser to provide an advantage for the filler to open the vacuum bag 12 or may include none of the these features. Specifically the vacuum bag 12 may be opened by cutting the vacuum bag 12 without use of a tear perforation 18.

In an alternative method, after the tray 14 and vials 16 are removed from the vacuum bag 12 by an operator, a rigid sheet (not shown) may be positioned onto the base side 16b of the vials 16. The operator or a robot may then invert the tray 14, vials 16 and rigid sheet and place the rigid sheet on a support surface (not shown) such that the base side 16b is resting on the rigid sheet. The rigid sheet is then moved out from under the vials 16 such that the base side 16b is resting on the support surface and the tray 14 maintains the vials 16 in their consolidated configuration. The tray 14 may then be vertically removed from the vials 16 such that the head side 16a is exposed and the vials 16 may be grasped for introduction onto an assembly line. Another alternative would be to insert the vials 16 into the tray 14 with their head side 16a proximate a floor 14a of the tray 14. When the vials 16 and tray 14 are ready to be removed from the vacuum bag 16, the vacuum bag 16 would be inverted with the base side 16b of the vials facing the support surface (not shown). The tray and vials would then be moved out of a tear in the bag 16 such that the base side 16b of the vials 16 are in facing engagement with the support surface. The tray 14 would then be vertically moved away from the vials 16 such that the head side 16a is exposed and the vials 16 may be grasped for introduction onto an assembly line.

Alternatively, referring to FIGS. 2-4, in operation, the plurality of vials 16 may be sterilized and positioned in the sterilized tray 14 with the head side 16a or base side 16b adjacent the floor 14a, potentially depending upon whether the vials 16 will be inserted into the assembly line manually or by a robot. The tray 14 with the stacked vials 16 positioned therein is inserted into the internal cavity 12a of the vacuum bag 12. The vacuum bag 12 is then transported to a sealing mechanism, which includes the clamp jaws 22, the vacuum probe 24 and the sealing jaws 26. The clamp jaws 22 close over the open end 12b and the vacuum probe 24, creating an air tight seal at the open end 12b. The vacuum probe 24 is connected to a vacuum source (not shown) and is actuated to evacuate air from the internal cavity 12a until a predetermined vacuum is reached. The vacuum bag 12 conforms to the exposed shape of the tray 14 and stacked vials 16 indicating a vacuum is being created within the vacuum bag 12. The pressure of the vacuum bag 12 on the external surfaces of the vials 16 and tray 14 preferably hold the vials 16 in the tray 14 such that the vials 16 do not rub against each other during movement or shipping. The peripheral flange 38 provides stiffness to the tray 14 so that the tray 14 is not crushed when the vacuum bag 12 is evacuated. When the predetermined vacuum is reached, the vacuum probe 24 is withdrawn from the open end 12b and the sealing jaws 26 are simultaneously closed over the open end 12b. The sealing jaws 26 create an air-tight seal across the open end 12b, preferably through a heat seal. The vacuum package system 10 is then irradiated and prepared for transport to an end user, typically a manufacturer who will fill the medical containers 16 with a medical product. Assuming the vacuum bag 12 is not breached during shipment, the vials 16 and tray 14 are sterile, pyrogen free and non-viable particulate matter free when they reach the manufacturer and may be introduced directly onto an assembly line in a clean environment.

The vacuum package system 10 generally prevents chafing and scratching of the plurality of vials 16 against one another during transport by consolidating the vials 16 due to the pressure applied to the tray 14 and vials 16 by atmospheric pressure outside the vacuum bag 12. Chafing or scratching of the vials 16 may produce unacceptable particles and damage surface finish making the vials 16 unsafe and useless for receipt of medical products. The vacuum package system 10 also preferably counteracts the impact of reduced atmospheric pressure, which the vacuum package system 10 may encounter during transportation by aircraft, during land transport at high elevations or in nearly any conditions where the vacuum package system 10 is exposed to reduced atmospheric pressure, as was described above. A typical sealed container that is filled with vials 16 may be subjected to reduced atmospheric pressure during aircraft or high elevation transportation that may be significant enough to cause an unvented package with approximately sea level pressure inside to expand to the point that seams are stressed and burst. Because the vials 16 of the vacuum package system 10 are stored under vacuum, the reduced atmospheric pressure has little or no effect upon the vacuum bag 12 and vials 16 of the preferred embodiments. Further, the use of the vacuum package system 10 provides a ready indicator of a breach in the vacuum bag 10 to the end user. If the vacuum bag 12 is breached during transport or prior to reaching the end user, the vacuum bag 12 will not thereafter cling or conform to the shape of the tray 14 and/or vials 16. Accordingly, an end user is aware that there has been a breach of the vacuum package system 10 and the sterile, pyrogen free and particulate matter free condition of the vials 16 may have been compromised. However, if the vacuum bag 12 is not breached, the end user is aware that the vials 16 are generally sterile, pyrogen free and non-viable particulate matter free and may be introduced directly into an assembly operation for filling the vials 16 with medical products.

When the unbreached vacuum package system 10 reaches a user, the user grasps the vacuum bag 12 on either side of the tear notch 18 and rips the vacuum bag 12 open. Inclusion of the tear notch 18 allows the vacuum bag 12 to be opened without the use of tools or the generation of particles that may contaminate the vials 16 during a cutting operation. The vacuum package system 10 is typically opened in a clean room to maintain sterility of the vials 16. The tray 14 and vials 16 are removed from the open end 12b and a sterile, pyrogen free and non-viable particulate matter free rigid sheet (not shown) that covers the open end of the tray 14 is placed on the assembly such that the base sides 16b of the vials 16 are in contact with the sheet. The entire assembly is inverted such that the vials 16 are resting on the sheet. The assembly is placed onto the support surface and the sheet is removed laterally from beneath the stacked vials 16, leaving the vials 16 resting on the surface on their base side 16b. The tray 14 is then removed vertically leaving the plurality of stacked vials 16 standing on the surface for manual insertion into the filling machine. Alternatively, the tray 14 is stacked with vials 16 having their base sides 16b adjacent the floor 14a. The tray 14 and stacked vials 16 are removed from the vacuum bag 12 and are positioned on the support surface with the floor 14a adjacent the surface. The vials 16 may then be removed directly from the tray 14 and placed onto an assembly line for filling the vials 16 with medical products, preferably by a robot. One having ordinary skill in the art will realize that the above-described methods of stacking and processing the vials 16 are not limiting and the vials 16 may be stacked in the tray 14 in nearly any configuration and processed in nearly any manner once the tray 14 and vials 16 are removed from vacuum bag 12 in preparation for the introduction of medical products therein. The above-described stacking and processing methods are merely provided as examples of typical stacking and processing techniques.

Figure 6:
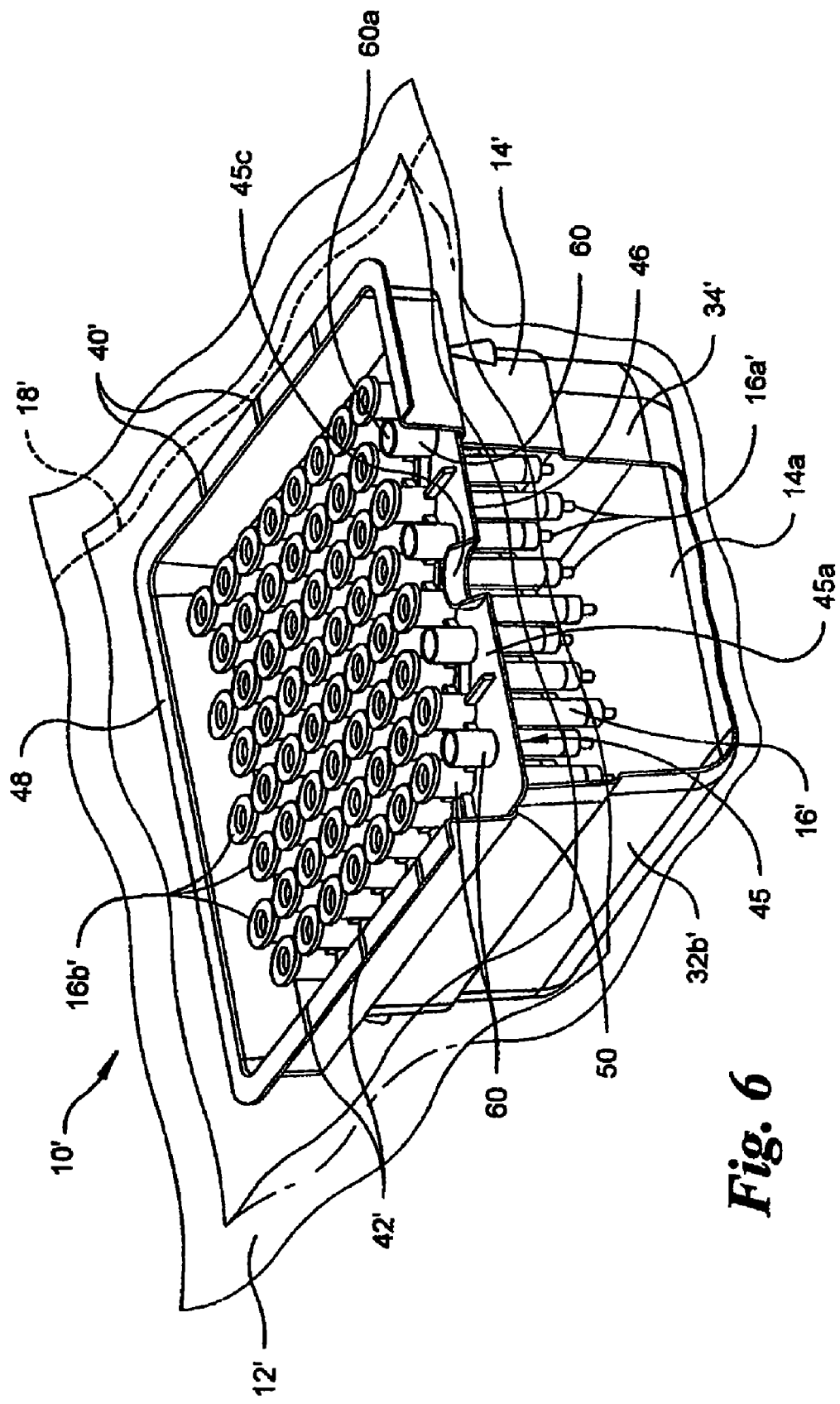
FIG. 6 is a top perspective, partial fragmentary view of a vacuum packaging system including a plurality of syringes mounted on a nesting plate in a tray that is positioned within a vacuum bag in accordance with a second preferred embodiment of the present invention.
Figure 7:
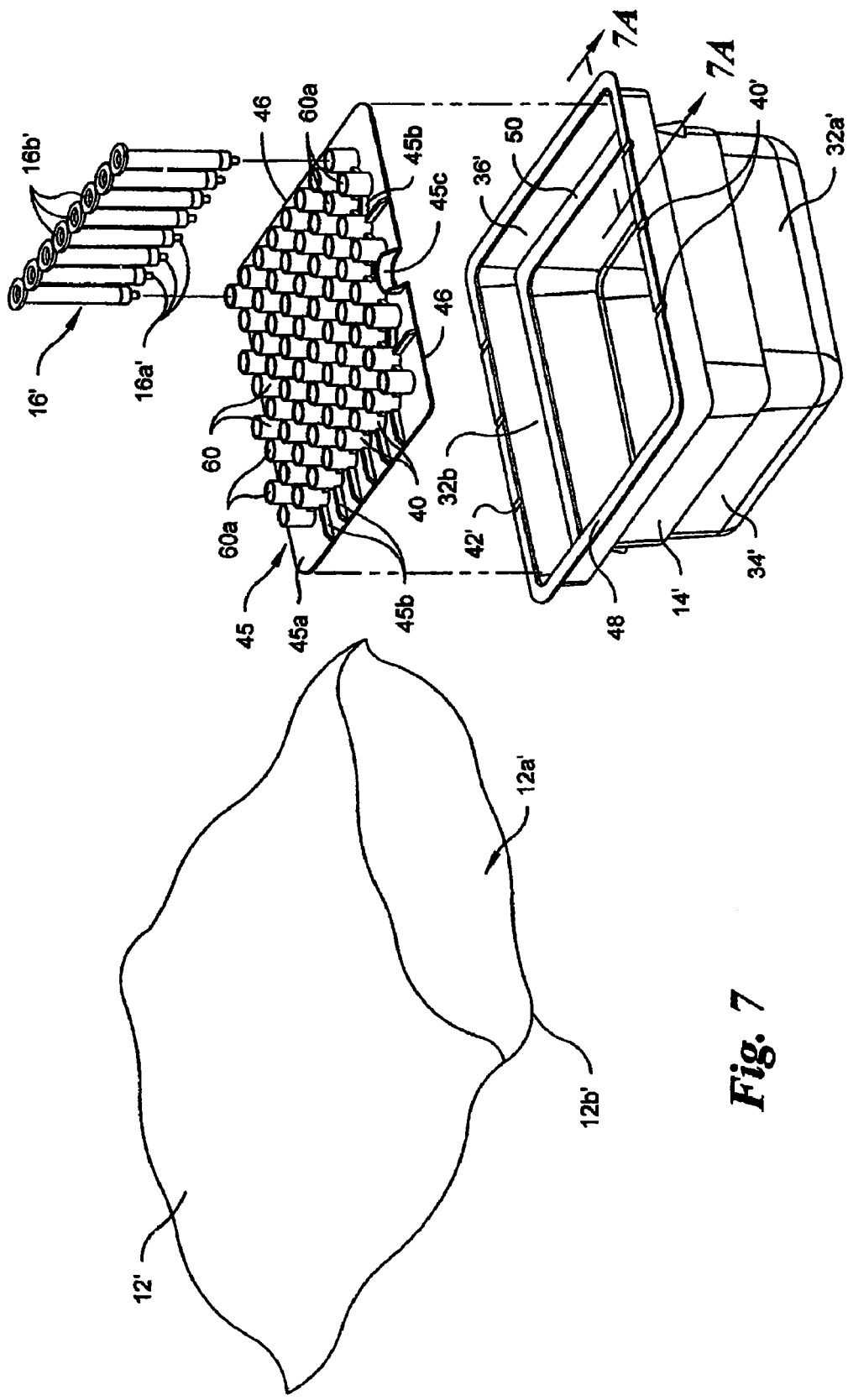
FIG. 7 is an exploded view of the vacuum packaging system shown in FIG. 6.
Figure 7A:
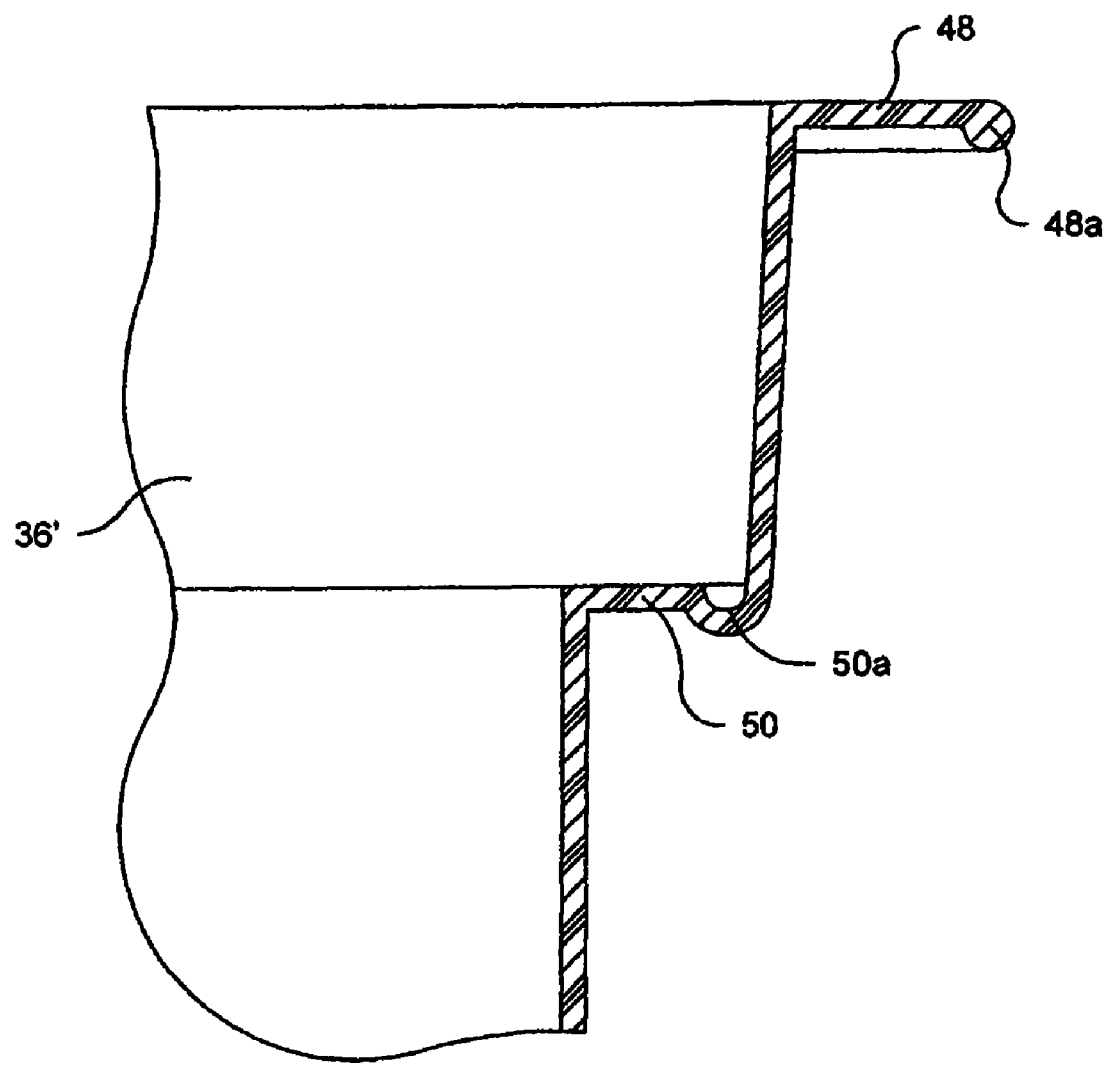
FIG. 7A is a partial cross-sectional view of the tray of the vacuum packaging system shown in FIG. 6, taken along line 7A-7A of FIG. 7.

Referring to FIGS. 6-7A, in a second preferred embodiment, like numerals are utilized to identify like elements and a prime symbol (') is utilized to distinguish like components of the vacuum package system 10' of the second preferred embodiment from the vacuum package system 10 of the first preferred embodiment. In the second preferred embodiment, the medical containers 16' are comprised of syringes 16' that are positioned within the tray 14' for shipping or other transport. The vacuum packaging system 10' preferably permits shipping of the syringes 16' in a ready-to-use condition that is sterile, pyrogen free and non-viable particulate matter free, similar to the above-described vacuum package system 10 of the first preferred embodiment. The syringes 16' have the head side 16a' and the base side 16b', with the base side 16b' including a flange.

In the second preferred embodiment, the tray 14' is constructed of an injection molded polymeric material to form the general size and shape of the tray 14'. The tray 14' is not limited to being injection molded using a polymeric material and may be constructed of a thermoformed plastic material or a machined material, as long as the tray 14' is able to take on its general size and shape and withstand the normal operating conditions of the tray 14'.

The syringes 16' are generally constructed of a high grade polymeric or plastic material that is desirable in the marketplace because of a high resistance to breakage, low chemical extractables and a reduced weight when compared to similar glass syringes. The syringes 16' are typically designed to be used in pre-filled applications and are packaged in generally rigid polymeric trays 14'. In the trays 14', the syringes 16' are preferably mounted in an upright orientation by a nesting plate 45, which is typically constructed of a generally rigid, polymeric material. The nesting plate 45 has a plurality of holes 60a defined by cylindrical sleeves 60. The cylindrical sleeves 60 preferably releasably receive one of the plurality of syringes 16' and hold an empty syringe 16' in a vertical orientation in the tray 14'. The syringes 16' are positioned in the cylindrical sleeves 60 such that the flange at the base end 16b' rests on a top end of the sleeves 60. The syringes 16' are preferably oriented, generally perpendicularly to a plane of a generally planar base 45a of the nesting plate 45. This arrangement of the syringes 16' in the tray 14' is generally known to one having ordinary skill in the art. The array of syringes 16' generally have common center to center distances such that robotic handling equipment is able to remove and insert the syringes 16' from and into the nesting plate 45.

Glass syringes 16' packed in the nesting plate 45 and tray 14', in the manner shown in FIG. 6, are typically sealed in the tray 14' with a permeable lid (not shown) that allows the penetration of a sterilant vapor and can be peeled back to gain access to the glass syringes 16'. This same packaging and sterilization method is not practical for polymeric syringes 16' because the polymeric material has a tendency to absorb the sterilant and release it very slowly. In addition, utilizing the permeable lid does not prevent the external surfaces of the tray 14' from being exposed to the external environment during shipping. Exposure of the external surfaces of the tray 14' to the external environment generally prevents an operator from introducing the tray 14' into a clean environment because of the potential for contamination. High quality polymeric or plastic syringes 16' can be effectively sterilized by irradiation, penetrating gamma or e-beam radiation and, therefore, do not need the permeable packaging. A non-permeable package, however, is subject to the effects of changing atmospheric pressure, much as was described above for the vacuum package system 10 of the first preferred embodiment. Part of the package function is to contain the syringes 16' in the nesting plate 45 within the tray 14' to reduce movement of the syringes 16' and maintain the syringes 16' in a sterile, pyrogen free and non-viable particulate matter free condition until they are ready to be filled with medical products. If a non-permeable package expands due to reduced atmospheric pressure encountered primarily during air shipment or alternate high elevation shipment, the package will no longer hold the syringes 16' in position in the nesting plate 45, potentially resulting in rubbing of the syringes 16' against the nesting plate 45 or bumping in to each other. A secondary effect is that the package may be stressed at weld points or other stress risers and may rupture during shipping. A rupture of the package would cause a leak and the sterility of the contents would likely be compromised.

A solution for this application is to apply a vacuum package using the flexible film or vacuum bag 12', as was described for the first preferred embodiment. A multi-layer film comprised of at least one layer with very low gas permeability is fashioned into the vacuum bag 12'. The tray 14' containing the syringes 16' mounted in the nesting plate 45 is placed into the vacuum bag 12' and the bag 12' is evacuated and sealed, as was described above. With the air removed, the bag 12' clings tightly to the tray 14' and the upper end or flanges of the syringes 16' holding them firmly in the nesting plate 45. The negative effects of reduced atmospheric pressure are counteracted because the bag 12' generally will not loosen its grip on the syringes 16' until the pressure on the inside of the bag 12' equals the pressure on the outside of the bag 12'. For this reason it is desirable to reach a level of vacuum inside the bag 12' at least equal or nearly equal to the pressure encountered in aircraft shipment which is typically eight inches of mercury (8 in. Hg) below standard atmospheric or equivalent to eight thousand feet (8,000 ft.) above sea level. Held tightly in the nesting plates 45, the syringes 16' are less likely to be scratched by contact with the nesting plate 45 and other packaging materials. The vacuum in the bag 12' also serves as a ready indicator of package integrity since even the slightest leak or breach will cause the bag 12' to relax, which will be visually apparent to an operator inspecting the bag 12'. A bag 12' with a leak would thus be readily identified visually as having been breached. Further, maintenance of the vacuum pressure in the bag 12' indicates that the tray 14' and its external surfaces have maintained their sterile, pyrogen free and non-viable particulate matter free condition.

In the second preferred embodiment, the nesting plate 45 includes the generally planar base 45a and reinforcing ribs 45b extending generally perpendicularly from the base 45a. The reinforcing ribs 45b preferably extend from peripheral edges 46 of the nesting plate 45 toward the cylindrical sleeves 60 to provide stiffness and strength to the planar base 45a. An arcuate shaped edge rib 45c also extends generally perpendicularly from the planar base 45a and defines an edge hole. The edge hole is preferably included in the nesting plate 45 such that a user is able to insert a finger or tool through the edge hole to remove the nesting plate 45 from the tray 14'. The edge rib 45c provides stiffness and strength for the base 45a proximate the edge hole. The edge hole and edge rib 45c are not limited to inclusion in the edge of the base 45a and may be positioned at nearly any location on the nesting plate 45 and are not limited for inclusion on the nesting plate 45. The cylindrical sleeves 60 preferably define holes 60a through the nesting plate 45 that are sized and shaped to accept the syringes 16'. The nesting plate 45 is not limited to the inclusion of the reinforcing ribs 45b or the cylindrical sleeves 60. For example, the nesting plate 45 may be constructed of a generally planar plate with holes formed therein for receipt of the syringes 16'. However, the cylindrical sleeves 60 and ribs 45b are preferred for inclusion in the nesting plate 45 to properly orient and space the syringes 16' relative to the nesting plate 45 and to provide strength and stiffness for the nesting plate 45 when the assembly is inserted into the internal cavity 12a' and the vacuum is drawn from the internal cavity 12a'.

In the second preferred embodiment, the tray 14' includes a mouth 48 and a lip 50 proximate the mouth 48. The mouth 48 preferably includes a rounded peripheral bulb 48a at its peripheral edge that provides stiffness to the mouth 48 and provides an arcuate surface for the vacuum bag 12' to engage when a vacuum is drawn on the internal cavity 12a'. A sharp edge at the rounded peripheral bulb 48a could potentially breach the bag 12' when a vacuum is drawn from the internal cavity 12a' exposing the tray 14' and syringes 16' to external air. The peripheral edge 46 of the nesting plate 45 is positioned on the lip 50 to support the nesting plate 45 within the tray 14' in an assembled configuration. The lip 50 is provided to vertically support the nesting plate 45 above the floor 14a' and to generally space the head side 16a' of the syringe 16' from the floor 14a'. The lip 50 is preferably integrally formed in the walls 32a', 32b', 34', 36' of the tray 14'. The lip 50 preferably includes a stiffening groove 50a that provides stiffness to the lip 50 and tray 14' such that the force of the bag 12' against the lip 50 does not significantly deform or crush the lip 50 or tray 14'. The tray 14' is not limited to inclusion of the lip 50 to support the tray 14' or the specific shape and configuration of the lip 50 including the stiffening groove 50a shown in the drawings. For example, the nesting plate 45 may be mechanically fastened, clipped, bonded or otherwise mounted to the tray 14'. In addition, the nesting plate 45 may include legs (not shown) that support the plate 45 above the floor 14a'.

In operation, the vacuum packaging system 10' of the second preferred embodiment is utilized in a similar manner to the vacuum packaging system 10 of the first preferred embodiment. A difference between the two systems is that, during operation, the nesting plate 45 is inserted into the tray 14' such that the peripheral edge 46 of the nesting plate 45 is positioned on the lip 50. The syringes 16' are then inserted into the holes 60a such that the flange on the base end 16b' is in facing engagement with the top of the cylindrical sleeve 60 and the head end 16a' is positioned proximate the floor 14a'. A lid (not shown) may be engaged with the mouth 48 of the tray 14' to close the mouth 48, however, the lid is not necessary for the operation of the vacuum packaging system 10', as will be understood by one having ordinary skill in the art. The tray 14' is positioned into the internal cavity 12a' of the vacuum bag 12' and the internal cavity 12a' is purged and evacuated to the predetermined vacuum pressure using the vacuum probe 24. The troughs 40', 42' provide a conduit for the purge gas and/or air to exit the tray 14' as the vacuum bag 12' collapses onto the mouth 48. However, the tray 14' is not limited to the inclusion of the troughs 40', 42' and may have a generally planar mouth 48 without significantly impacting the vacuum packaging system 10'. The packaging, opening and use of the vacuum packaging system 10' of the second preferred embodiment is otherwise similar to the use of the vacuum packaging system 10 of the first preferred embodiment, as will be understood by one having ordinary skill in the art.

Figure 9:
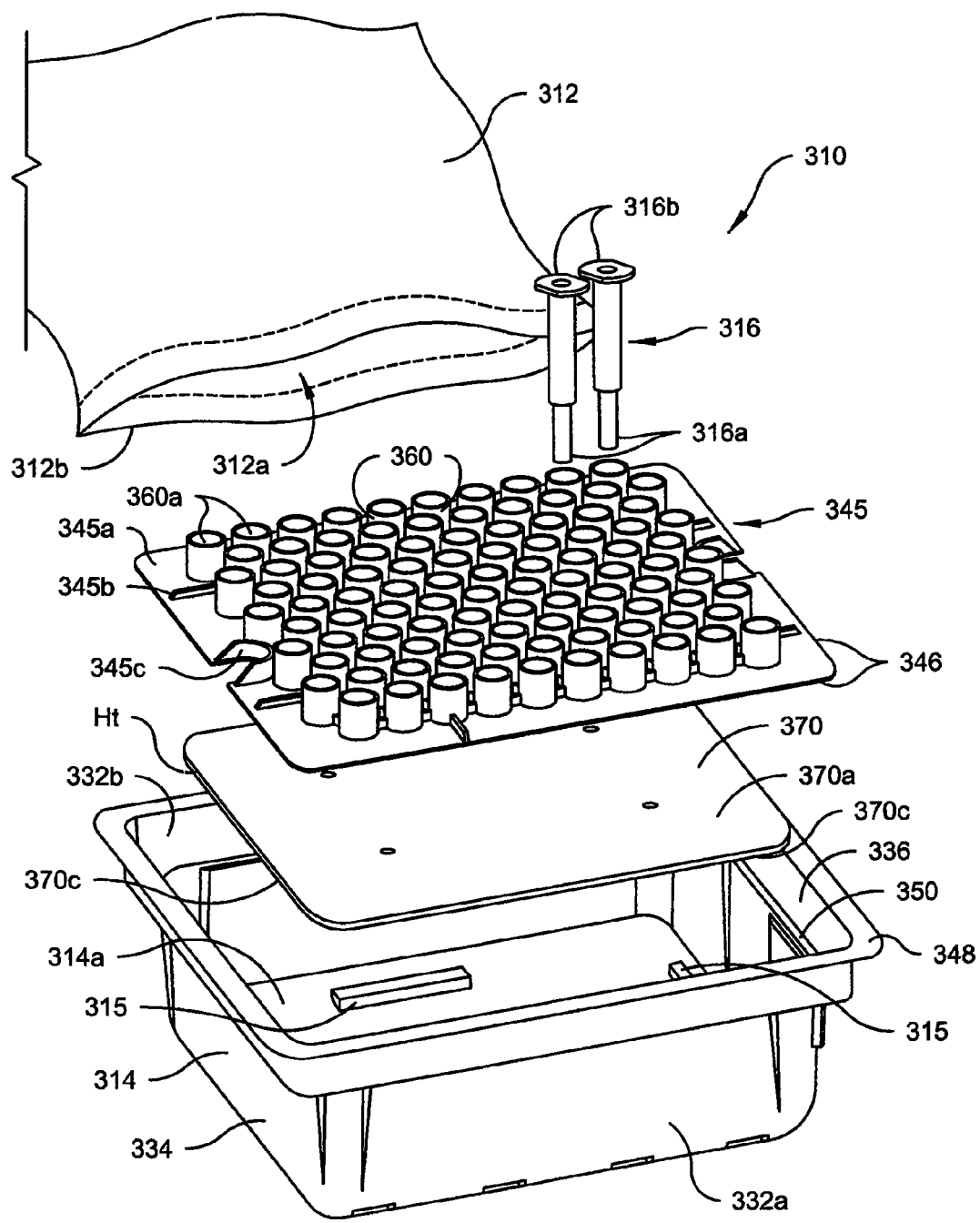
FIG. 9 is a perspective view of a partially exploded vacuum packaging system for holding a plurality of syringes mounted on a nesting plate in a tray that is positioned within a vacuum bag in accordance with a third preferred embodiment of the present invention.

Referring to FIG. 9, a third preferred embodiment of the vacuum packaging system 310 is shown, including like reference numerals to indicate like elements throughout. The vacuum packaging system 310 of the third preferred embodiment is substantially similar in structure and operation to the second embodiment described above. In the third preferred embodiment, the vacuum packaging system 310 is used for transporting a plurality of medical containers that are preferably comprised of syringes 316. Each medical container 316 includes a head side 316a and a base side 316b, similar to that disclosed in the second preferred embodiment. A tray 314 receives and supports the medical container 316 within a nesting plate 345, as in the second preferred embodiment. The tray 314 includes opposing first and second sidewalls 332a, 332b, opposing front and rear walls 334, 336 and a bottom floor 314a. The walls 332a, 332b, 334, 336 extend generally vertically from the floor 314a of the tray 314 and a lip 350 extends around the interior of the tray 314 and preferably includes a stiffening groove (not shown). Furthermore, as in the second preferred embodiment, an air impervious flexible film or vacuum bag 312, which has an open end 312b and an internal cavity 312a, completely surrounds the tray 314 and the medical containers 316. The internal cavity 312a is evacuated to and maintained at a predetermined vacuum level below atmospheric pressure, as is described above in the second preferred embodiment. Similar to the previous embodiments, the mouth 348 of the tray 314 may or may not include one or more troughs (not shown) to provide a conduit for the purge gas and/or air to exit the tray 314 as the vacuum bag 312 collapses.

One difference between the third preferred embodiment and the second preferred embodiment is that the third preferred embodiment includes at least one platform 370 that generally extends parallel to the floor 314a. The at least one platform 370 is perpendicularly spaced from the floor 314a by a predetermined distance when the platform 370 is placed within the tray 314. The predetermined distance is due to the height of at least two spaced-apart protrusions 315 that orthogonally extend upwardly from the floor 314a and are in contact with the bottom surface of the platform 370 when the platform 370 is positioned in the tray 314. The platform 370 is preferably rectangular in shape when viewed from above or below and includes a top surface 370a, an opposing bottom surface (not shown), and four sidewalls 370c extending generally orthogonally from the top and bottom surfaces. The platform 370 is preferably sized such that the sidewalls 370c are generally in abutting contact with an interior surface of the walls 332a, 332b, 334, 336 of the tray 314 when the platform 370 is positioned on top of or against the bottom floor 314a of the tray 314. Preferably, the at least one platform 370 is removably mountable to the tray 314, but it is understood that the at least one platform 370 may be fixedly attached to the floor 314a of the tray 314 via a fastening mechanism (not shown), such as adhesive, one or more fasteners, friction fitting or the like.

In operation, the at least one platform 370 allows a manufacturer or user to lessen a pressure load on the nesting plate 345 caused by the pressure of the vacuum bag 312 by using the medical containers 316 to at least partially support the pressure of the vacuum bag 312. Specifically, when the at least one platform 370 is positioned within the tray 314 and the medical containers 316 and nesting plate 345 are placed within the tray 314, at least one of a head side 316a and a base side 316b of at least one of the medical containers 316 is a abutting contact with the top surface 370a of the platform 370. Thus, as the internal cavity 312a is evacuated to and maintained at a predetermined vacuum level below atmospheric pressure, bending, deforming or warping of the nesting plate 345, as a result of the pressure load, is reduced or avoided as at least one of the medical containers 316 absorbs at least a portion of the pressure load applied to the system 310. Specifically, the at least one platform 370 contacts one of a head side 316a and a base side 316b of at least one of the syringes 316 and transmits the pressure load applied by the outside air pressure on the vacuum bag 312 through that at least one syringe 316, thereby relieving at least a portion of the pressure load on the nesting plate 345. However, as is understood by those skilled in the art, a small amount of pressure pre-load can still be permitted on the nesting plate 345, and may be beneficial, so that the nesting plate 345 will remain secure within the final system 310 and not be loose or easily knocked out of place.

The platform 370 is preferably formed of a high strength, light weight material, such as a polymeric material. However, other materials, such as a metallic material or a fiber glass material may be used. The sidewalls 370c preferably have a predetermined thickness Ht approximately equal to the distance between the floor 314a of the tray 314 and the head side 316a or base side 316b of the medical containers 316 when the medical containers 316 are positioned in the tray 314. Alternatively, the system 310 may include two or more platforms 370 that are sized and shaped to fit within the tray 314 to relieve at least a portion of the pressure load on the nesting plate 345. For example, the platform 370 may be comprised of two separate platforms that are sized and shaped so that when they are placed side-by-side, they are generally the size and shape of the at least one platform 370. Alternatively, the platform 370 may be comprised of two or more vertically stackable platforms, such that the height Ht can be modified to accommodate the size of various medical containers.

Figure 10A:
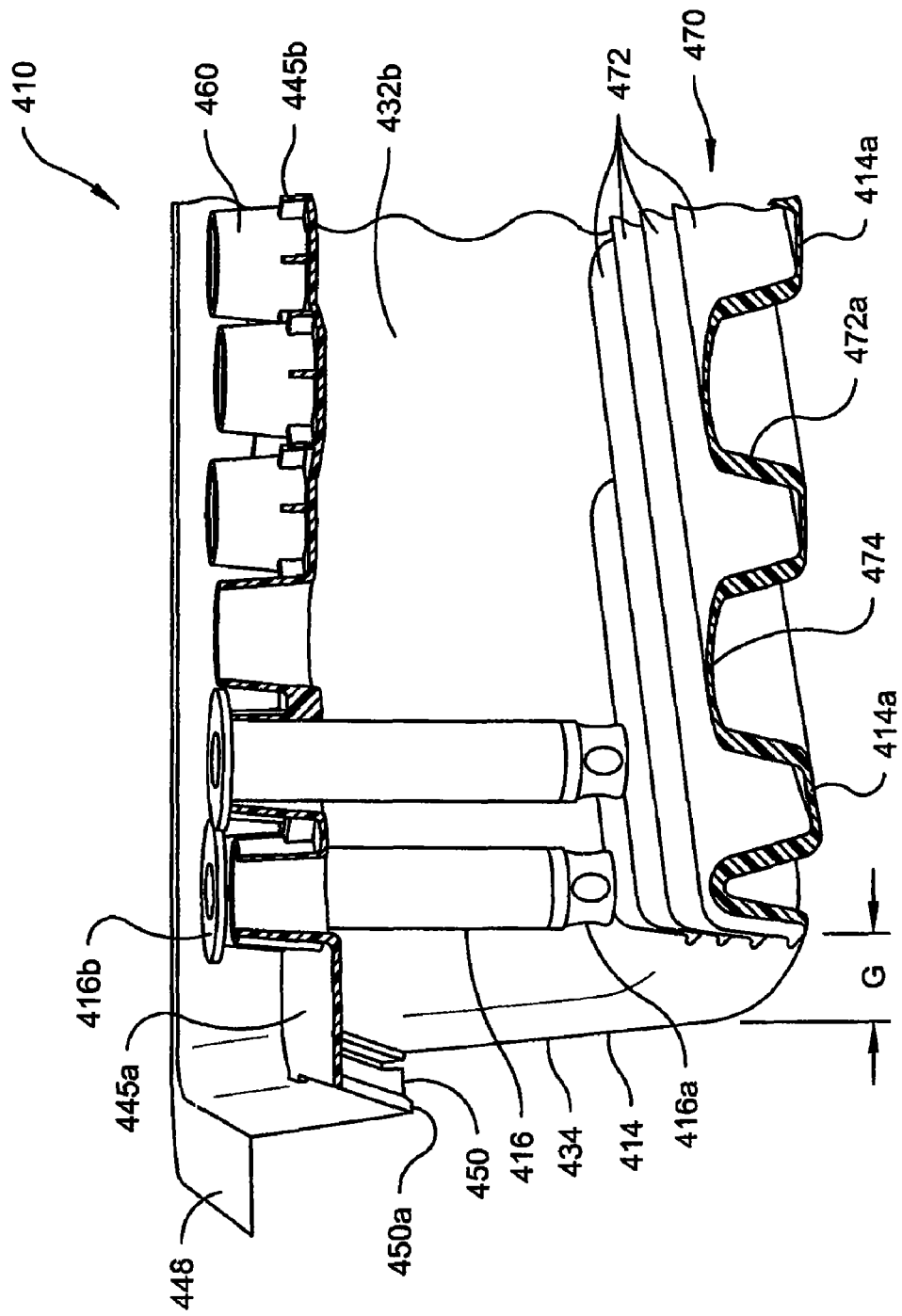
FIG. 10A is a cross-sectional elevation view of a portion of a vacuum packaging system for holding a plurality of syringes mounted on a nesting plate in a tray that is positioned within a vacuum bag in accordance with a fourth preferred embodiment of the present invention.
Figure 10B:
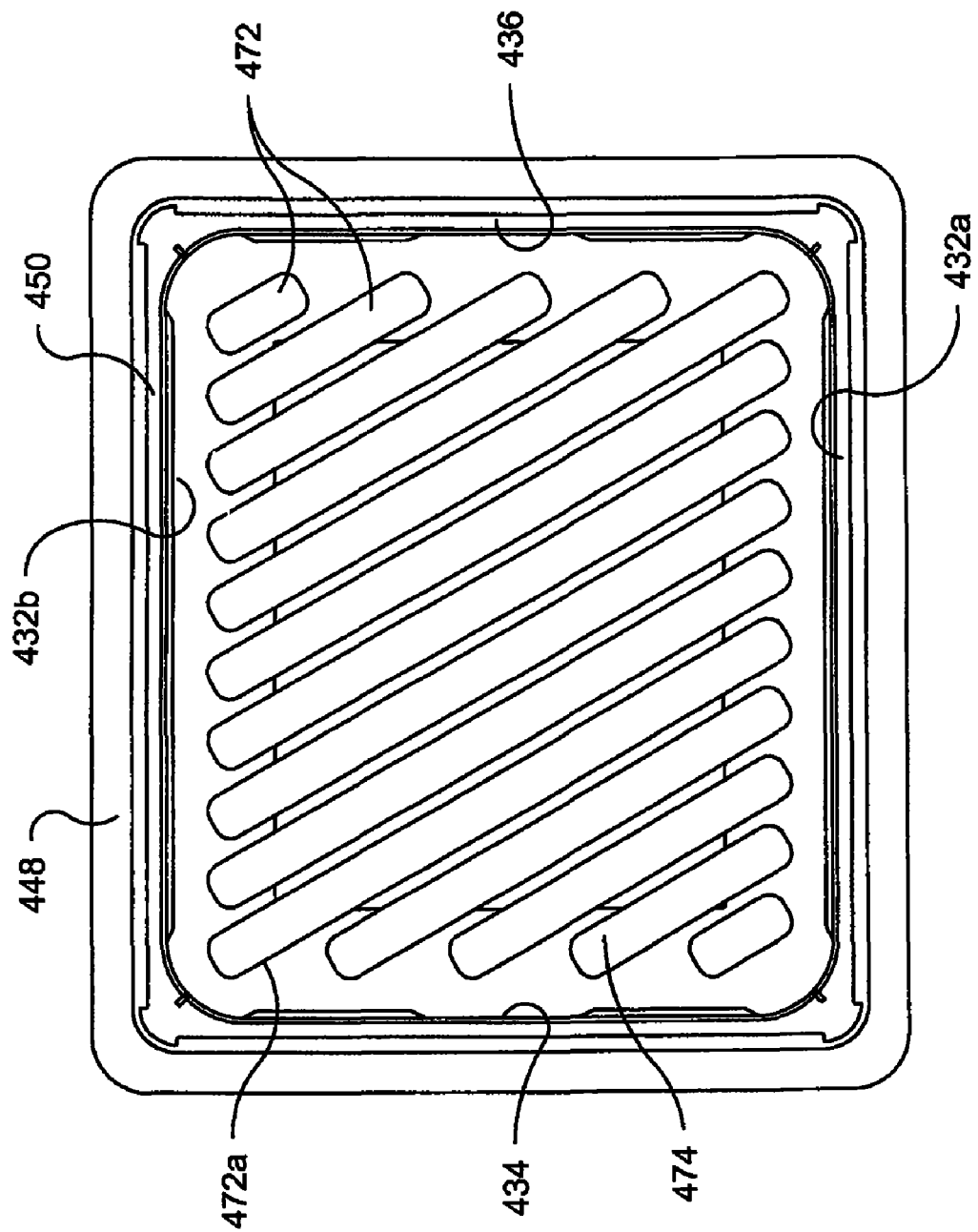
FIG. 10B is a top plan view of the tray of the vacuum packaging system shown in FIG. 10A.
Figure 11A:
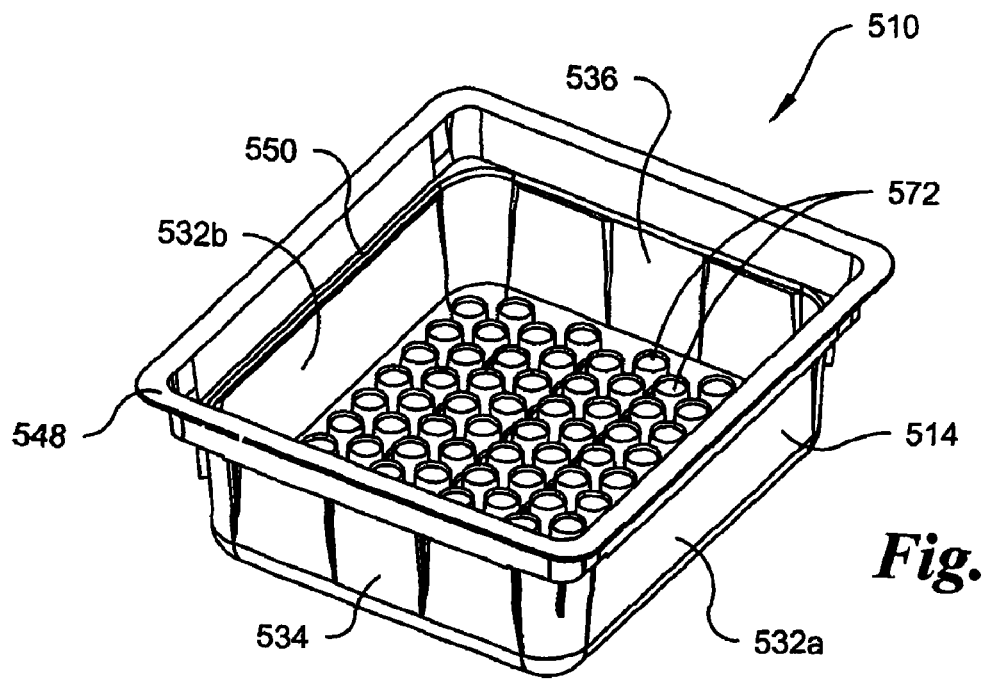
FIG. 11A is a top perspective view of a tray of a vacuum packaging system for holding a plurality of syringes mounted on a nesting plate in the tray that is positioned within a vacuum bag in accordance with a fifth preferred embodiment of the present invention.
Figure 11B:
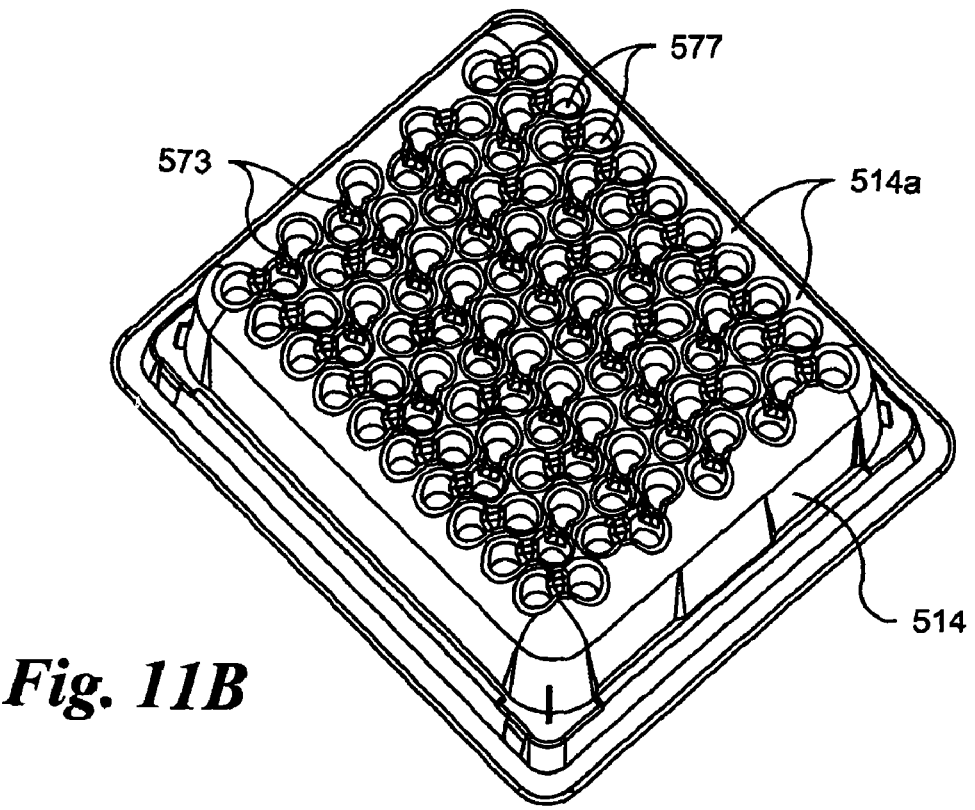
FIG. 11B is a bottom perspective view of the tray of the vacuum packaging system shown in FIG. 11A.
Figure 11C:
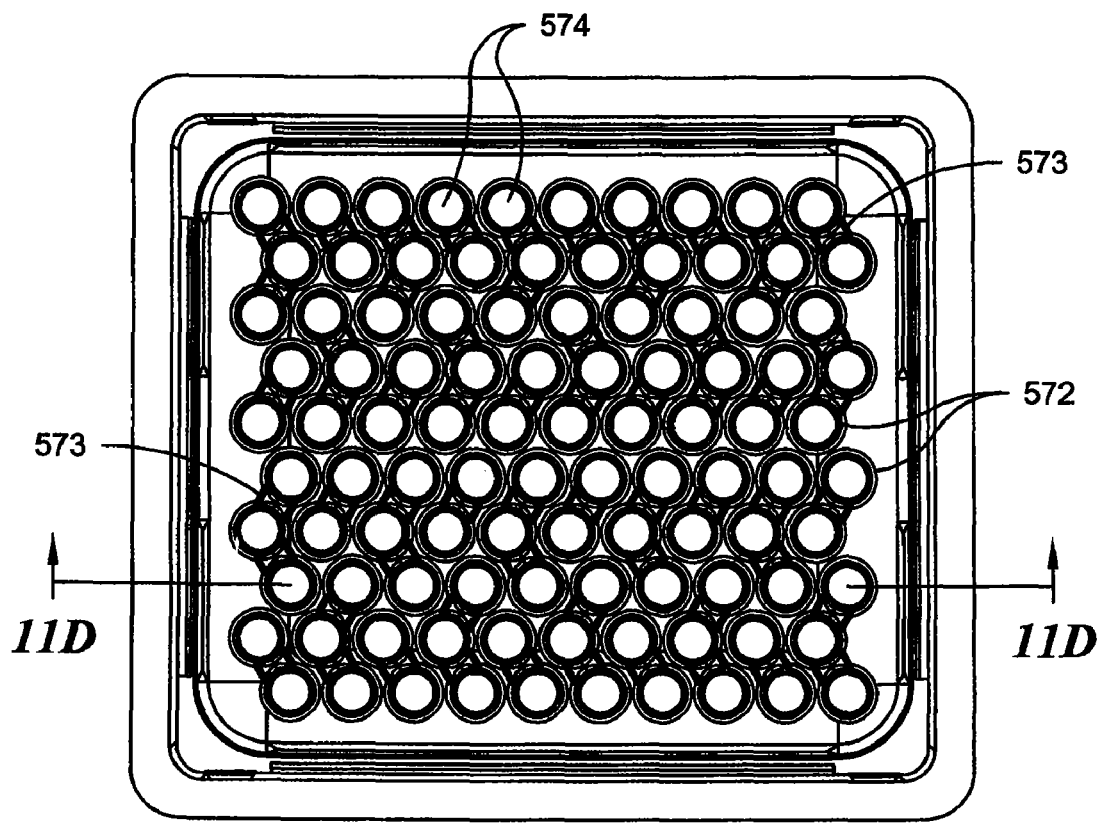
FIG. 11C is a top plan view of the tray of the vacuum packaging system shown in FIG. 11A.
Figure 11D:
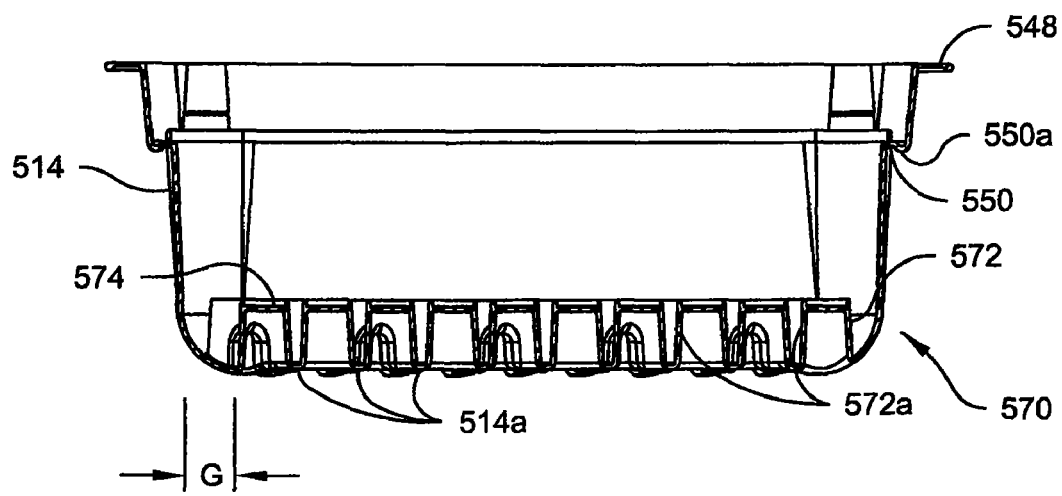
FIG. 11D is a cross-sectional elevation view of the tray of the vacuum packaging system shown in FIG. 11A, taken along line 11D-11D of FIG. 11C.

Referring to FIGS. 10A-10B, a fourth preferred embodiment of the vacuum packaging system 410 is shown, including like referenced numerals to indicate like elements throughout. The vacuum packaging system 410 of the fourth preferred embodiment is substantially similar in structure and operation to the third embodiment described above, although certain structure is omitted from the drawings for clarify.

One primary difference between the fourth preferred embodiment and the third preferred embodiment is that the platform 470 of the fourth preferred embodiment includes a plurality of spaced-apart projections 472. Each projection 472 includes a side surface 472a that extends generally perpendicular to the floor 414a of the tray 414 and a top surface 474 that generally extends parallel to the floor 414a of the tray 414. Thus, a top surface of the platform 470 is perpendicularly spaced from the floor 414a by a predetermined distance. The predetermined distance is due to the height of the side surfaces 472a. Further, the plurality of projections 472 are preferably diagonally oriented or angled with respect to the walls 432a, 432b, 434, 436 of the tray 414. The projections 472 are preferably integrally formed with the floor 414a of the tray 414. However, it is understood by those skilled in the art that the projections 472 may be removably mounted within the tray 414. The plurality of projections 472 are preferably sized such that one of the head 416a and the base side 416b of at least one medical containers 416 contacts a top surface of a portion of one of the projections 472 to help reduce or lessen the pressure load on the nesting plate 445 as a result of the vacuum pressure. The plurality of projections 472 is generally wave-like in shape when viewed from the side such that each projection 472 is separated by a flat portion of the bottom floor 414a of the tray 414. Preferably, a space or gap G exists between a sidemost point of each projection 472 and an interior surface of each of the walls 432a, 432b, 434, 436 of the tray 414. The gap G corresponds to the portion of the tray 445 that extends from the lip 450 to the first set of medical containers 416.

Referring to FIGS. 11A-11D, a fifth preferred embodiment of the vacuum packaging system 510 is shown, including like referenced numerals to indicate like elements throughout. The vacuum packaging system 510 of the fifth preferred embodiment is substantially similar in structure and operation to the third and fourth embodiments described above, although certain structure is omitted from the drawings for clarify.

One primary difference between the fifth preferred embodiment and the fourth preferred embodiment is that the platform 570 includes a plurality of projections 572 that are generally circular in shape when viewed from above or below. The plurality of projections 572 are preferably connected in groups of two or three by a bridge 573 that is angularly displaced with respect to the walls 532a, 532b, 534, 536 of the tray 514. Each of the projections 572 preferably includes at least one depression 574 formed in a top surface thereof. The at least one depression 574 is generally sized and shaped to receive at least a portion of one of the head side and the base side of at least one medical containers when the medical containers are positioned in the tray 514. Sidewalls 572a of each of the plurality of projections 572 are slightly angled when viewed from the side. A portion of the floor 514a of the tray 514 separates each of the plurality of projections 572. When viewing the tray 514 from below (FIG. 11B), the plurality of projections 572 appear to extend toward a midsection of the tray 514 and create a plurality of corresponding cup-shaped recesses or craters 577.

Figure 12A:
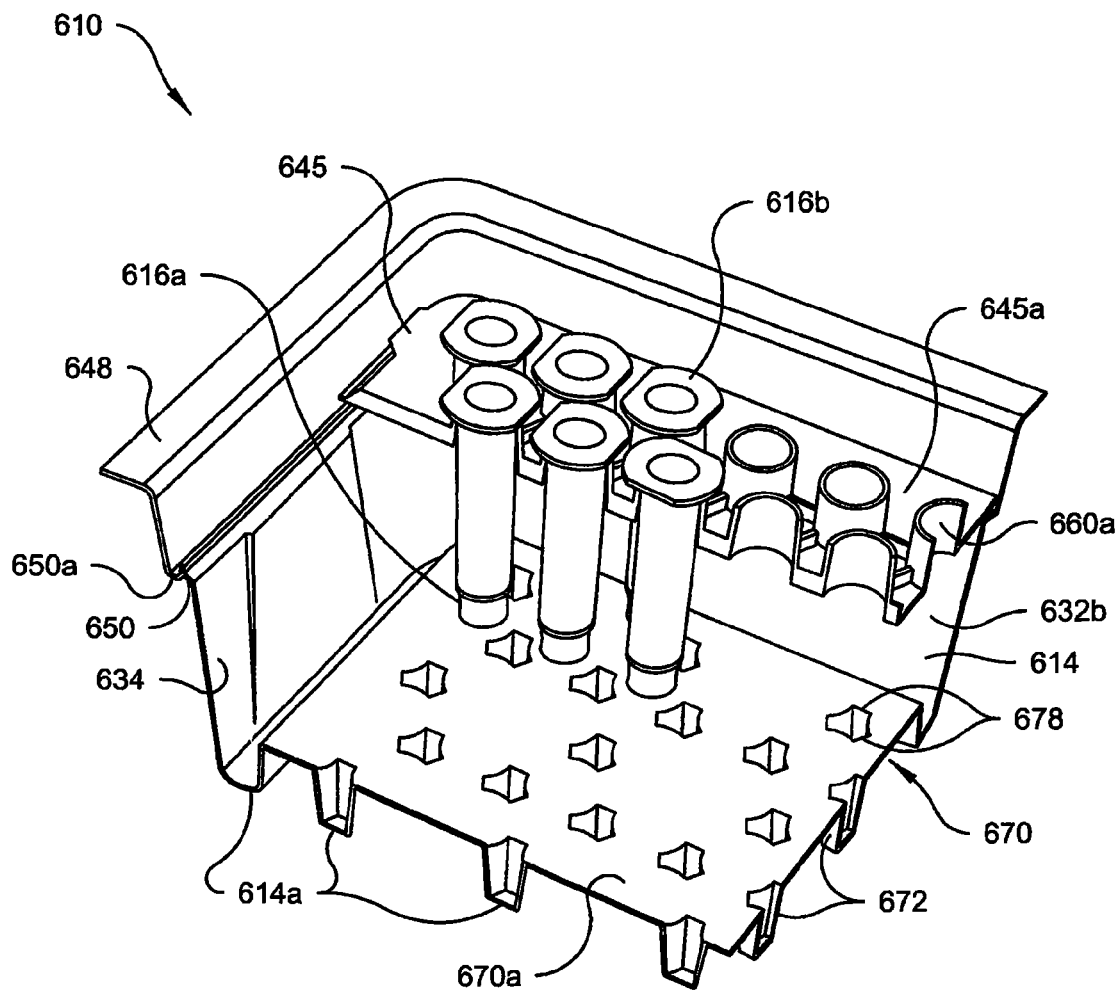
FIG. 12A is a perspective view of a portion of a vacuum packaging system for holding a plurality of syringes mounted on a nesting plate in a tray that is positioned within a vacuum bag in accordance with a sixth preferred embodiment of the present invention.
Figure 12B:
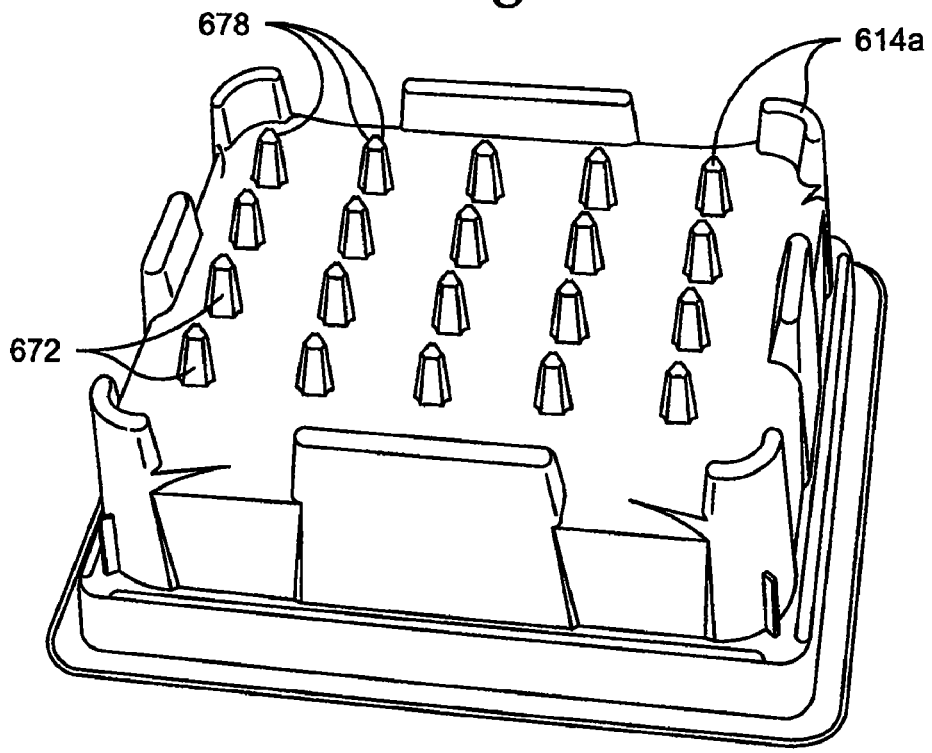
FIG. 12B is a bottom perspective view of the tray of the vacuum packaging system shown in FIG. 12A.
Figure 12C:
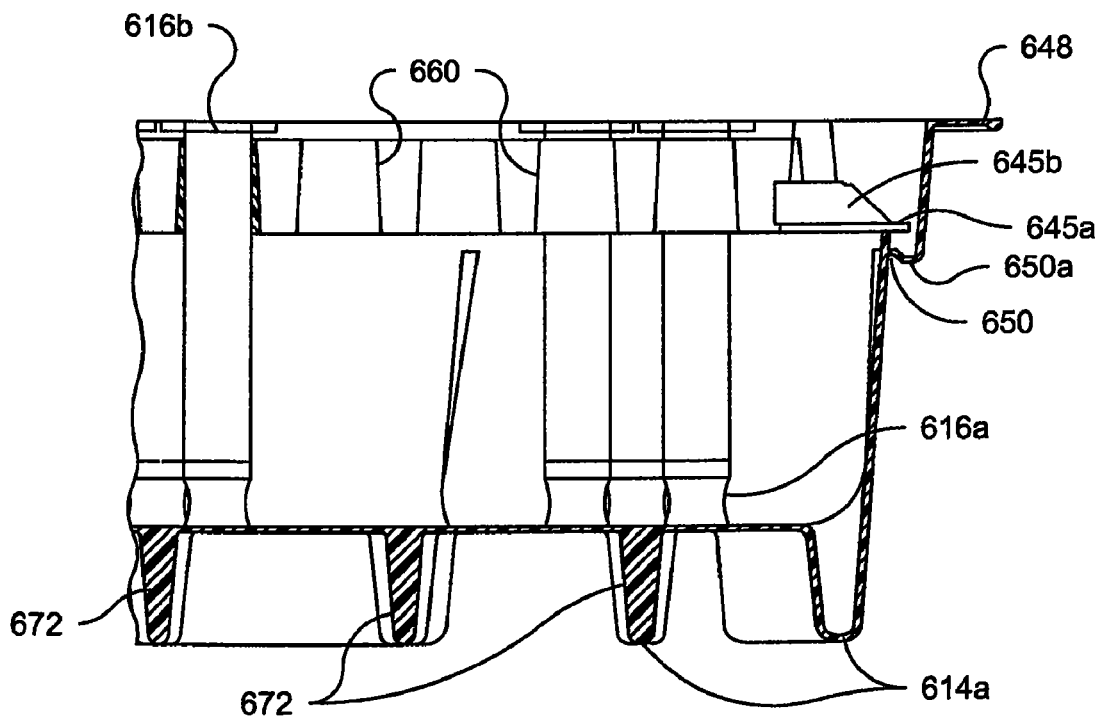
FIG. 12C is a cross-sectional elevation view of a portion of the vacuum packaging system shown in FIG. 12A.

Referring to FIGS. 12A-12C, a sixth preferred embodiment of the vacuum packaging system 610 is shown, including like referenced numerals to indicate like elements throughout. The vacuuming packaging system 610 of the sixth preferred embodiment is substantially similar in structure and operation to the embodiments described above, although certain structure is omitted from the drawings for clarify.

A primary difference between the sixth preferred embodiment and the embodiments described above is that the at least one platform 670 includes a plurality of projections 672 that extend orthogonally away from the nesting plate 645 when the nesting plate 645 is positioned in the tray 614. Specifically, the platform 670 is integrally formed with the bottom floor 614a of the tray 614. A top surface 670a of the platform 670 is spaced a predetermined distance from the bottom floor 614a to provide a foundation to contact with one of a head side 616a and a base side 616b of at least one medical container 616 to help reduce or alleviate the pressure on the nesting plate 645 caused by the vacuum.

Contrary to the third through fifth embodiments described above, the plurality of projections 672 of the system 610 do not directly contact one of a head side 616a and a base side 616b of at least one medical container 616. Instead, one of a head side 616a and a base side 616b of at least one medical container 616 contacts the top surface 670a while the plurality of projections 672 help support the top surface 670a above the supporting surface (not shown) on which the tray 614 is placed. When viewed from above or below, each projection 672 includes at least one but preferably three generally blunt and angularly displaced prongs 678 to provide stability to the projections 672.

Referring to FIGS. 13A and 13B, an seventh preferred embodiment of the vacuum packaging system 710 is shown, including like referenced numerals to indicate like elements throughout. The vacuum packaging system 710 of the seventh preferred embodiment is substantially similar in structure and operation to the sixth preferred embodiment described above, although certain structure is omitted from the drawings for clarify.

A primary difference between the seventh preferred embodiment and the sixth preferred embodiment is that the platform 770 of the seventh preferred embodiment includes a plurality of spaced-apart depressions 774 that are spaced around and/or between the plurality of projections 772 that extend downwardly away from the nesting plate (not shown) when the nesting plate 745 is positioned in the tray 714. The depressions 774 are preferably sized and shaped to conform to one of a head side and a base side of at least one medical container when the medical container is positioned in the tray 714. As is understood by those skilled in the art, the size, location and number of depressions 774 may be modified by the manufacturer depending upon the users needs.

Referring to FIGS. 14A-14D, an eighth preferred embodiment of the vacuum packaging system 810 is shown, including like reference numerals to indicate like elements throughout. The vacuum packaging system 810 of the eighth preferred embodiment is substantially similar in structure and operation to the embodiments described above. As a result, certain structure of the eighth preferred embodiment is omitted from FIGS. 14A-14D for clarity and brevity.

Similar to the previous embodiments, the system 810 is designed for transporting a plurality of medical containers (not shown), such as syringes, each of which include a head side (not shown) and a base side (not shown). A tray or tub 814 receives and/or supports the medical containers in an assembled configuration (similar to FIG. 10A). The tray 814 includes opposing first and second side walls 832a, 832b, opposing front and rear walls 834, 836, and a bottom floor 814a. The walls 832a, 832b, 834, 836 extend generally perpendicularly from the bottom floor 814a of the tray 814 to a top edge 814b thereof. Similar to the second and third preferred embodiments, for example, the system 810 includes a nesting plate (not shown) removably mountable in the tray 814. The nesting plate includes a top surface, which generally faces the external environment of the tray 814 when the nesting plate is placed in an assembled configuration (see FIG. 6), an opposing bottom surface, which generally faces an interior of the tray 814 when the nesting plate is placed in the assembled configuration, and plurality of generally cylindrical and spaced-apart sleeves (not shown). Each of the plurality of sleeves preferably receives one of the plurality of medical containers. In addition, an air impervious flexible film (not shown) defines an internal cavity (not shown). The air impervious flexible film completely surrounds the tray 814 and the medical containers and the internal cavity is evacuated to and maintained at a predetermined vacuum level below atmospheric pressure.

Figure 14A:
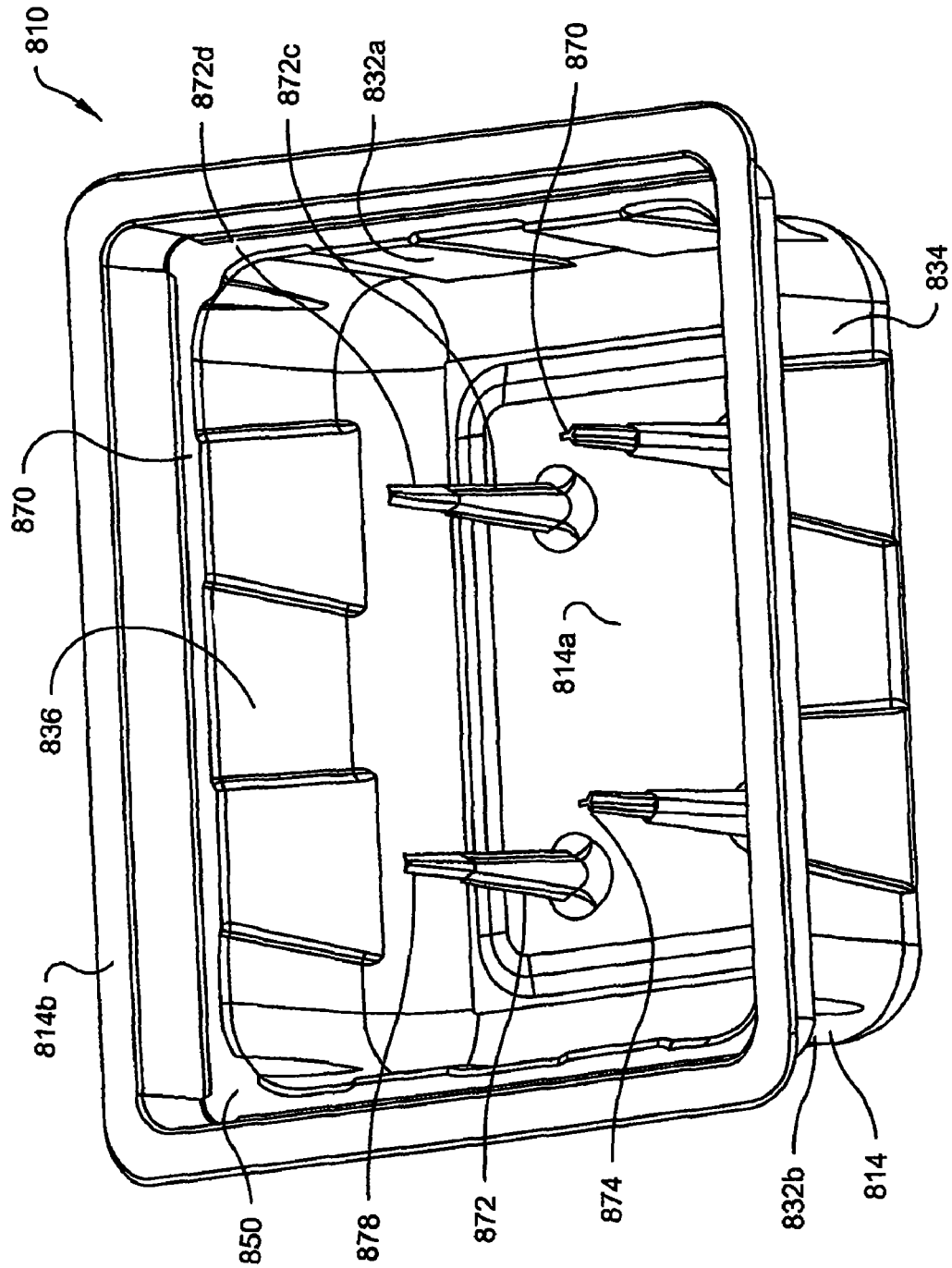
FIG. 14A is a top perspective view of a tray of a vacuum packaging system for holding a plurality of syringes mounted on a nesting plate in the tray that is positioned within a vacuum bag in accordance with an eight preferred embodiment of the present invention.
Figure 14B:
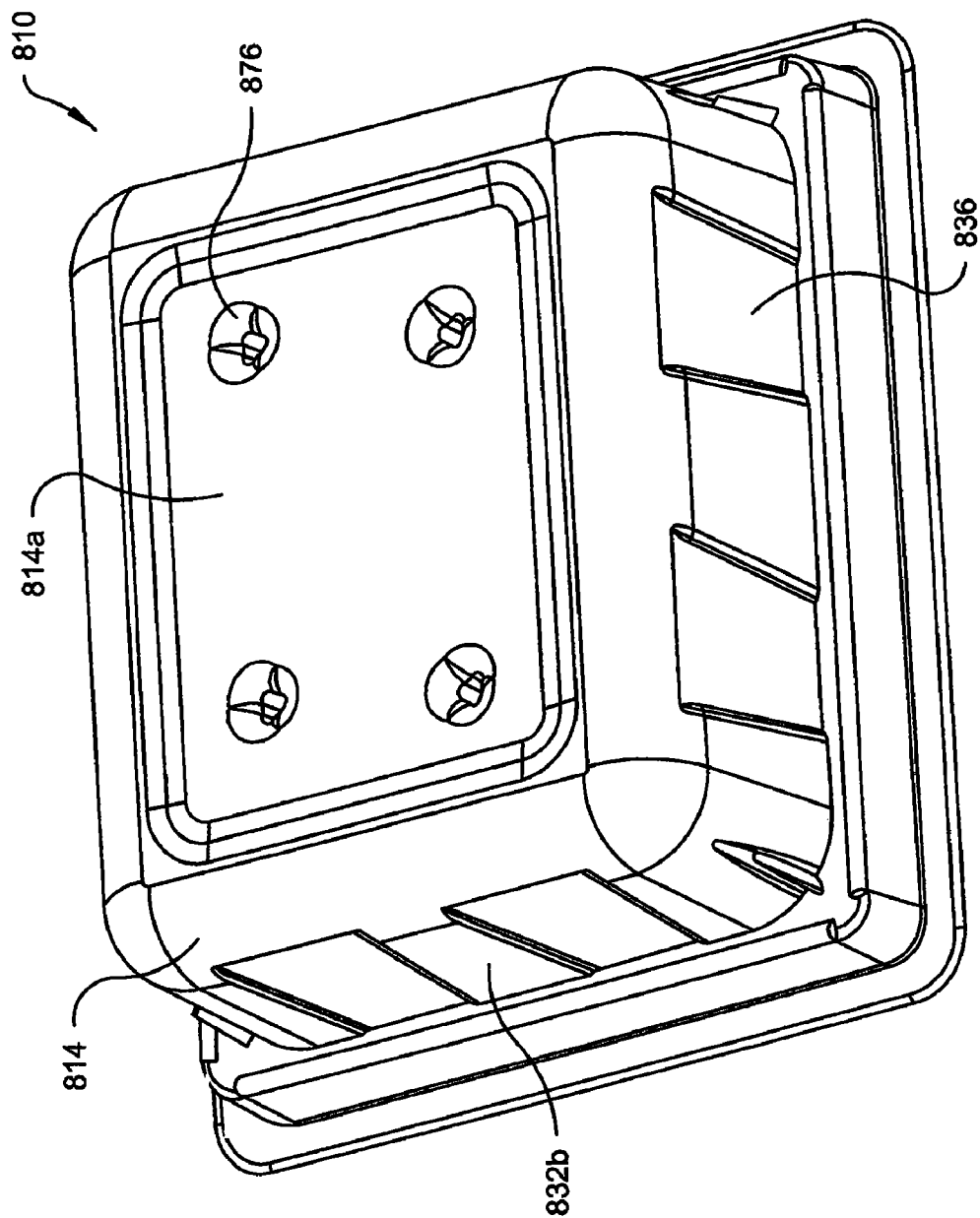
FIG. 14B is a bottom perspective view of the tray of the vacuum packaging system shown in FIG. 14A.
Figure 14C:
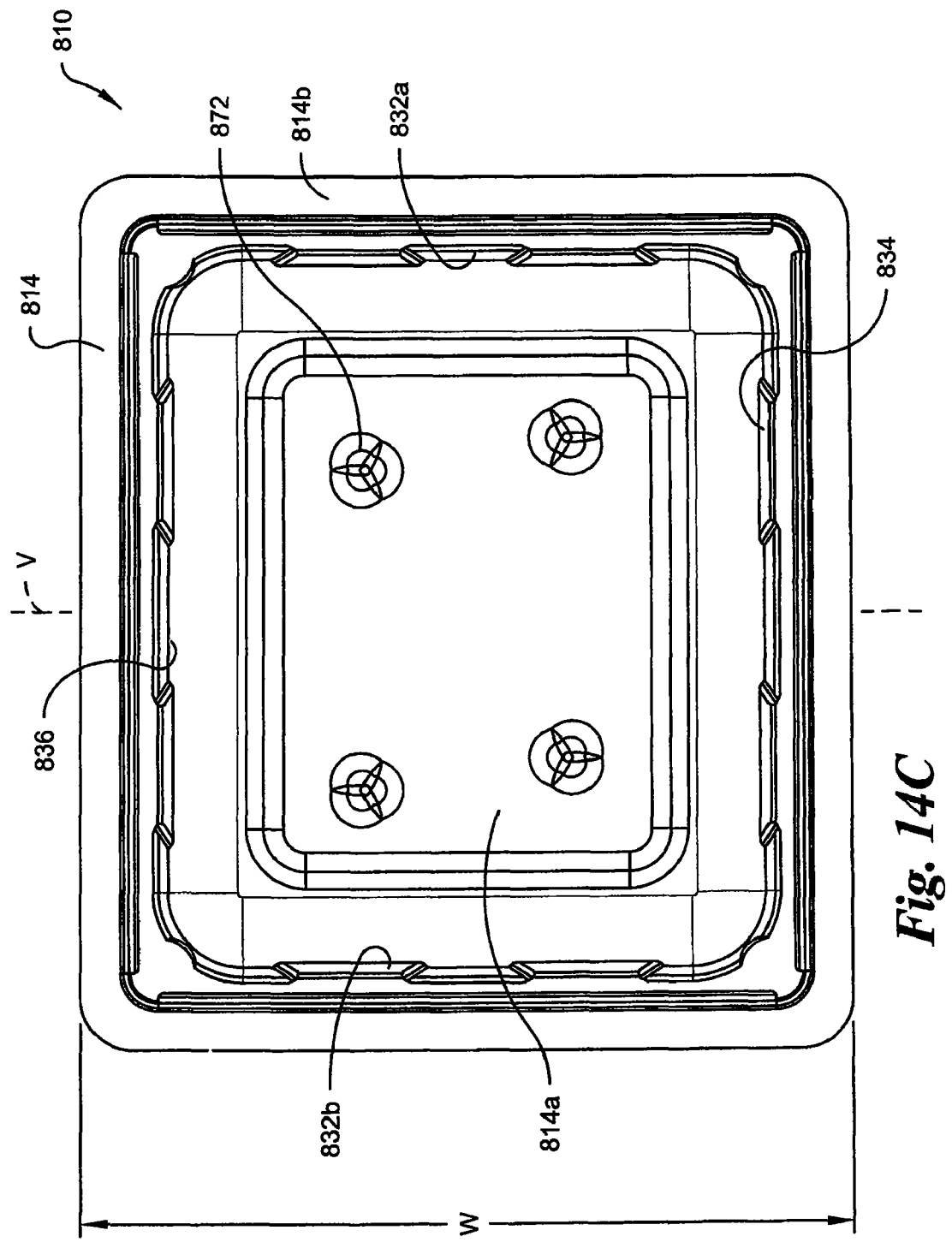
FIG. 14C is a top plan view of the tray of the vacuum packaging system shown in FIG. 14A.
Figure 14D:
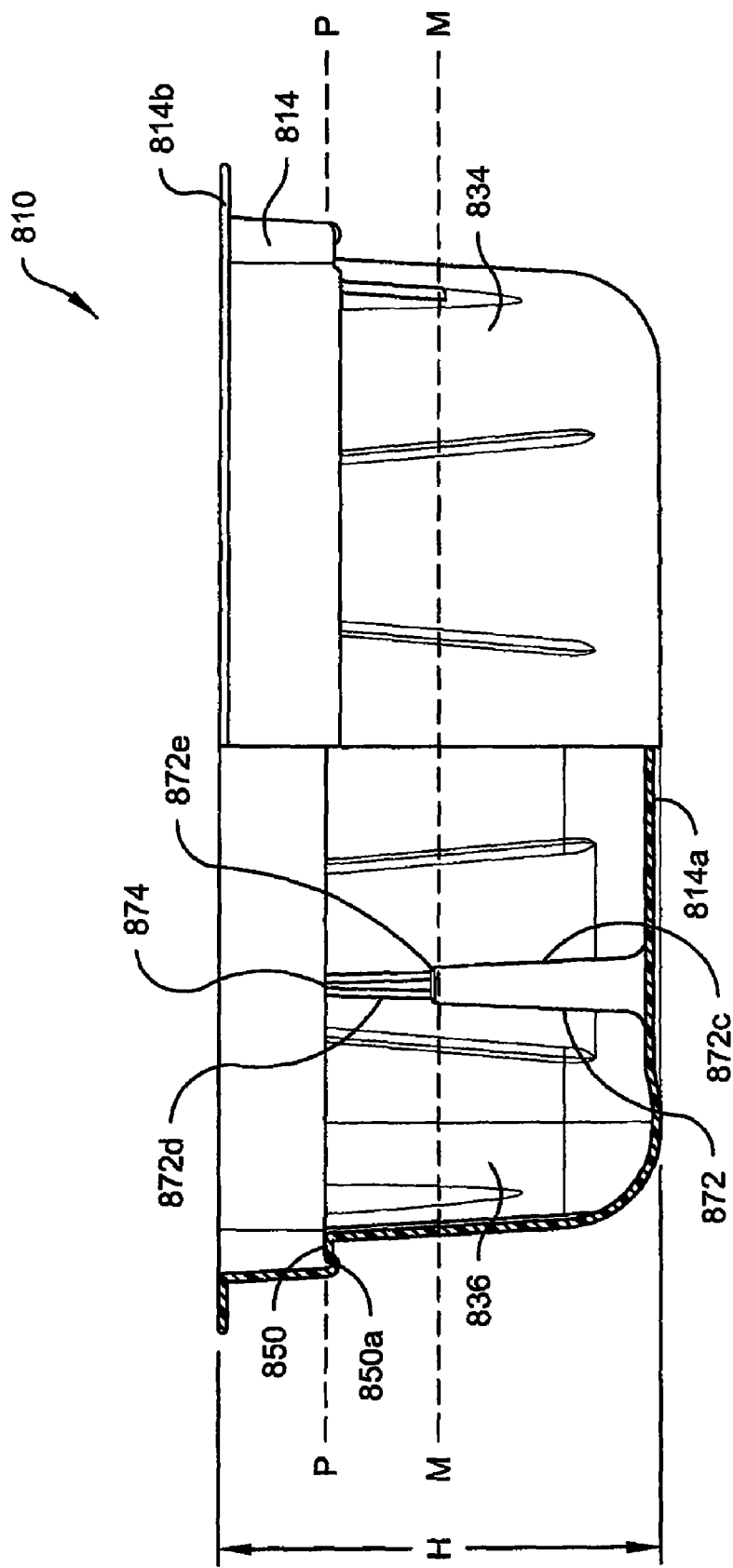
FIG. 14D is a partial cross-sectional elevation view of the tray of the vacuum packaging system shown in FIG. 14A

A primary difference between the eighth preferred embodiment and the embodiments described in detail above is that the system 810 includes a support surface or platform 870 within the tray 814 that extends generally parallel to and spaced a predetermined distance from the bottom floor 814a of the tray 814. When the system 810 is the assembled configuration (similar to that shown in FIG. 6), the support surface 870 receives and supports the nesting plate. As with the previous embodiments and as seen in FIG. 14D, the tray 814 has a height H that extends from the bottom floor 814a to the top edge 814b thereof. A vertical midpoint M of the height H of the tray 814 is defined as a point equidistantly spaced from the bottom floor 814a and the top edge 814b of the tray 814. Preferably, the support surface 870 is located above the vertical midpoint M and/or proximate the top edge 814b of the tray 814 with respect to the vertical midpoint.

In the preferred embodiment, the support surface 870 includes a plurality of support members or projections 872 that extend generally perpendicularly from the bottom floor 814a of the tray 814. In the present embodiment, the support surface 870 includes four spaced-apart support members 872 each including an enclosed planar first or top surface 874 forming a portion of the support surface 870 and an opposing second or open end 876 (FIG. 14B) proximate the bottom floor 814a of the tray 814 such that each support member 872 is generally hollow. Each support member 872 has a generally frusto-conical shape. As seen in FIGS. 14A-14C, when viewing the tray 814 from above or below, the support members 872 are at least slightly off-set or skewed with respect to a central vertical plane V that is generally parallel to a width W of the tray 814. Each support member 872 has a first portion 872c proximate the bottom floor 814a separated from a second portion 872d by a step or ledge 872e. As seen in FIG. 14A, both the first and second portions 872c, 872d have a generally "Y" shape, with the first portion 872c having a larger cross-sectional area than the second portion 872d. Further, each support member 872 includes at least one but preferably three generally blunt and angularly displaced prongs 878 to provide stability to the support member 872. The size, shape and configuration of the support members 872 allow multiple trays 814 to be stacked for storage or transportation purposes.

As seen in FIGS. 14A, 14C and 14D, the support surface 870 further includes a lip or ledge 850 that extends around at least a portion of each of the walls 832a, 832b, 834, 836 of the tray 814. As with several of the previous embodiments, the nesting plate includes a peripheral edge that is positioned on or above the lip 850 to support the nesting plate within the tray 814 in the assembled configuration. Likewise, the lip 850 preferably includes a stiffening groove 850a that provides stiffness to the lip 850 and tray 814 such that the force of the air impervious flexible film against the lip 850 does not significantly deform or crush the lip 850 or tray 814. As seen in FIG. 14D, the top surface 874 of each support member 872 and the lip 850 are generally co-planar and define a horizontal support plane P that extends a predetermined distance below the top edge 814b of the tray 814.

In the assembled configuration, the head side or tips of the medical containers dangle or are suspended a predetermined distance away from or above the bottom floor 814a of the tray 814. Specifically, when the air impervious flexible film is placed around the tray 814 and is then evacuated to and maintained at a predetermined vacuum level below atmospheric pressure, the air impervious flexible film pushes downwardly on the tray 814 and the base side of the medical containers. However, the support surface 870 receives, absorbs and/or distributes at least a portion of the force created by the vacuum. Thus, the head side of each medical container is left dangling or suspended above the bottom floor 814a of the tray 814 and the medical containers are protect and avoid damage when the vacuum is applied.

It will be appreciated by those skilled in the art that changes could be made to the preferred embodiments of the vacuum package system described above without departing from the broad inventive concept thereof. It is understood, therefore, that this invention is not limited to the particular embodiments disclosed, but is intended to cover modifications within the spirit and scope of the present application.

We claim:

1. A vacuum packaging system for transporting a plurality of medical containers comprising:

a plurality of medical containers, each medical container including a head side and a base side;

a tray that receives and supports the medical containers, the tray including opposing first and second sidewalls, opposing front and rear walls and a bottom floor, the walls extending generally perpendicularly from the bottom floor of the tray to a top edge thereof;

a nesting plate removably mountable in the tray, the nesting plate including a top surface, a bottom surface and a plurality of generally cylindrical sleeves, each of the plurality of sleeves receiving one of the plurality of medical containers;

a support surface within the tray extending generally parallel to and spaced a predetermined distance above the bottom floor of the tray, the support surface including a lip extending inwardly from a portion of each of the sidewalls, the front wall and the rear wall and a plurality of spaced-apart support members extending generally perpendicularly from the bottom floor of the tray, a top surface of each support member and a top surface of the lip being generally co-planar such that both the top surface of the lip and the top surface of each support member directly receive and support the bottom surface of the nesting plate; wherein each support member includes an enclosed first end forming a portion of the support surface and an open second end proximate the bottom floor of the tray such that each support member is generally hollow; and an air impervious flexible film defining an internal cavity, the air impervious flexible film completely surrounding the tray and the medical containers, the internal cavity being evacuated to and maintained at a predetermined vacuum level below atmospheric pressure.

2. The vacuum system of claim 1, wherein the nesting plate includes a generally planar base and reinforcing ribs extending generally perpendicularly from the base, the cylindrical sleeves defining holes in the base.

3. The vacuum packaging system of claim 1, wherein the medical containers are comprised of syringes.

4. The vacuum packaging system of claim 1, wherein the head side of each medical container is spaced a predetermined distance away from the bottom floor of the tray in the assembled configuration.

5. The vacuum packaging system of claim 1, wherein each support member has a first potion proximate the bottom floor separated from a second portion by a ledge.

6. The vacuum packaging system of claim 1, wherein each support member includes three angularly spaced-apart prongs that extend outwardly therefrom.

7. A vacuum packaging system for transporting a plurality of medical containers comprising:

a plurality of medical containers, each medical container including a head side and a base side;

a tray that receives and supports the medical containers, the tray including opposing first and second sidewalls, opposing front and rear walls and a bottom floor, the walls extending generally perpendicularly from the bottom floor of the tray to a top edge thereof, the tray having a height measured from the bottom floor to the top edge, a vertical midpoint of the tray defined as a point equidistantly spaced from the bottom floor to the top edge of the tray;

a support surface within the tray extending generally parallel to and spaced a predetermined distance above the bottom floor of the tray, the support surface having a plurality of spaced-apart support members extending generally perpendicularly from the floor of the tray, a top surface of each support member extending generally parallel to the bottom floor of the tray and being located along the height of the tray between the top edge and the vertical midpoint, wherein each support member includes an enclosed first end forming a portion of the support surface and an open second end proximate the bottom floor of the tray such that each support member is generally hollow;

a nesting plate removably mountable in the tray, the nesting plate including a top surface, a bottom surface and a plurality of generally cylindrical sleeves, each of the plurality of sleeves receiving one of the plurality of medical containers, wherein the support surface receives and supports the nesting plate and the nesting plate includes a peripheral edge that is positioned on a lip extending around at least a portion of each of the walls of the tray to support the nesting plate within the tray in the assembled configuration; and an air impervious flexible film defining an internal cavity, the air impervious flexible film completely surrounding the tray and the medical containers, the internal cavity being evacuated to and maintained at a predetermined vacuum level below atmospheric pressure.

8. The vacuum system of claim 7, wherein the nesting plate includes a generally planar base and reinforcing ribs extending generally perpendicularly from the base, the cylindrical sleeves defining holes in the base.

9. The vacuum packaging system of claim 7, wherein the head side of each medical container is spaced a predetermined distance away from the bottom floor of the tray in the assembled configuration.

10. The vacuum packaging system of claim 7, wherein the medical containers are comprised of syringes.

11. The vacuum packaging system of claim 7, wherein each support member has a first potion proximate the bottom floor separated from a second portion by a ledge.

12. The vacuum packaging system of claim 7, wherein each support member includes three angularly spaced-apart prongs that extend outwardly therefrom.

* * * * *